United States Patent
Yamashita et al.

(10) Patent No.: US 8,987,406 B2
(45) Date of Patent: Mar. 24, 2015

(54) CYCLIC POLYPHENYLENE ETHER ETHER KETONE COMPOSITION AND METHOD FOR PRODUCING THE SAME

(75) Inventors: Kohei Yamashita, Nagoya (JP); Shunsuke Horiuchi, Nagoya (JP); Koji Yamauchi, Nagoya (JP)

(73) Assignee: Toray Industries, Inc., Tokyo (JP)

( * ) Notice: Subject to any disclaimer, the term of this patent is extended or adjusted under 35 U.S.C. 154(b) by 0 days.

(21) Appl. No.: 13/501,613

(22) PCT Filed: Dec. 24, 2010

(86) PCT No.: PCT/JP2010/073268
§ 371 (c)(1),
(2), (4) Date: Jun. 6, 2012

(87) PCT Pub. No.: WO2011/081080
PCT Pub. Date: Jul. 7, 2011

(65) Prior Publication Data
US 2012/0259086 A1 Oct. 11, 2012

(30) Foreign Application Priority Data

Dec. 28, 2009 (JP) ................................. 2009-297278
Aug. 30, 2010 (JP) ................................. 2010-191971

(51) Int. Cl.
| | | |
|---|---|---|
| C08G 8/02 | (2006.01) | |
| C08G 14/00 | (2006.01) | |
| C07D 323/00 | (2006.01) | |
| C07D 321/00 | (2006.01) | |
| C08G 65/40 | (2006.01) | |
| C08G 65/48 | (2006.01) | |
| C08L 71/00 | (2006.01) | |

(52) U.S. Cl.
CPC ............ C07D 323/00 (2013.01); C07D 321/00 (2013.01); C08G 65/4012 (2013.01); C08G 65/4081 (2013.01); C08G 65/48 (2013.01); C08G 2650/34 (2013.01); C08G 2650/40 (2013.01); C08L 71/00 (2013.01)
USPC ....................................................... 528/125

(58) Field of Classification Search
CPC ........... C08G 2650/34; C08G 2650/40; C08G 65/4012; C08G 65/4081
USPC ....................................................... 528/125
See application file for complete search history.

(56) References Cited

U.S. PATENT DOCUMENTS

| | | | | |
|---|---|---|---|---|
| 5,194,561 A | * | 3/1993 | Fischer et al. ................. | 528/125 |
| 5,264,520 A | | 11/1993 | Mullins et al. | |
| 5,264,538 A | | 11/1993 | Mullins et al. | |
| 5,856,421 A | * | 1/1999 | Schmidhauser ............... | 528/125 |
| 2007/0013108 A1 | * | 1/2007 | Monsheimer et al. ........ | 264/482 |
| 2010/0137531 A1 | * | 6/2010 | Horiuchi ........................ | 525/537 |
| 2012/0165501 A1 | * | 6/2012 | Kaiho et al. .................. | 528/373 |

FOREIGN PATENT DOCUMENTS

| | | |
|---|---|---|
| CN | 1443762 | 9/2003 |
| CN | 1556085 | 12/2004 |
| CN | 101519399 A | 9/2009 |
| EP | 0413257 A2 | 2/1991 |
| WO | WO2005030836 A1 | 4/2005 |

OTHER PUBLICATIONS

Brunelle (Macrocycles for the synthesis of high molecular weight polymers, New Methods of Polymer Synthesis, Chapman and Hall, 1995).*
Brunelle (Journal of Polymer Science: Part A: Polymer Chmistry, vol. 46, 1151-1164, 2008).*
International Search Report dated Apr. 5, 2011, application No. PCT/JP2010/073268.
Chen, M., et al., Large-Sized Macrocyclic Monomeric Precursors of Poly (ether ether ketone): Synthesis and Polymerization, Macromolecules, 1996, vol. 29, No. 16, p. 5502-5504 Scheme 1-2, Compound 5.
Chen, M.F. et al., Concise synthesis and characterization of 30-membered macrocyclic monomer for poly (ether ether ketone), Macromolecular Chemistry and Physics, 1996, vol. 197, No. 12, p. 4069-4078 Scheme 2, Compound 5.

(Continued)

*Primary Examiner* — Liam J Heincer
(74) *Attorney, Agent, or Firm* — Ratner Prestia

(57) ABSTRACT

A cyclic poly (phenylene ether ether ketone) composition includes not less than 60% by weight of a cyclic poly (phenylene ether ether ketone) represented by the following Formula (I), which is characterized in that the cyclic poly (phenylene ether ether ketone) is a mixture of cyclic poly (phenylene ether ether ketone)s having different repeating numbers (m) and the composition has a melting point of not higher than 270° C.; and a method of producing a poly (phenylene ether ether ketone) characterized by heat-polymerizing the cyclic poly (phenylene ether ether ketone) composition:

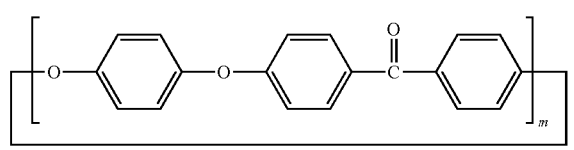

(I)

where m represents an integer of 2 to 40.

20 Claims, No Drawings

(56) References Cited

OTHER PUBLICATIONS

Qi, Y.H. et al., Synthesis of cyclic precursors of poly (ether ether ketone), Polymer Bulletin (Berlin), 1999, vol. 42, No. 3, p. 245-249 Scheme 2.
Supplementary European Search Report dated Nov. 2, 2012, application No. EP10840936.
Xie, D. et al., "Synthesis and Ring-Opening Polymerization of Single-Sized Aromatic Macrocyles for Poly (Rylene Ether)s", Macromolecules, American Chemical Society, Washington, DC, vol. 30, No. 17, Aug. 25, 1997, pp. 4814-4827, XP000696087.
Database WPI Week 200524, Thomson Scientific, London, GB; AN 2005-224028, XP002686384, Dec. 22, 2004.
Database WPI Week 200425, Thomson Scientific, London, GB; AN 2004-258064, XP002686385, Sep. 24, 2003.

* cited by examiner

CYCLIC POLYPHENYLENE ETHER ETHER KETONE COMPOSITION AND METHOD FOR PRODUCING THE SAME

CROSS REFERENCE TO RELATED APPLICATIONS

This application is the U.S. National Phase application of PCT International Application No. PCT/JP2010/073268, filed Dec. 24, 2010, and claims priority to Japanese Patent Application Nos. 2009-297278, filed Dec. 28, 2009 and 2010-191971, filed Aug. 30, 2010, the disclosures of all of which are incorporated herein by reference in their entireties for all purposes.

FIELD OF THE INVENTION

The present invention relates to a composition comprising a cyclic poly(phenylene ether ether ketone) and a production method thereof. More particularly, the present invention relates to a cyclic poly (phenylene ether ether ketone) composition comprising not less than 60% by weight of a cyclic poly (phenylene ether ether ketone), which is characterized by having a low melting point and excellent processability at a low temperature.

BACKGROUND OF THE INVENTION

Recently, aromatic cyclic compounds are drawing attention its application/development potential as a high-performance material or functional material based on the properties arising from the cyclic structure (e.g., as a compound having clathrating capacity and as a effective monomer in the synthesis of a high-molecular-weight linear polymer by ring-opening polymerization) as well as for its structure-derived specificity. Cyclic poly (phenylene ether ether ketone)s are also noteworthy in the same manner since they belong to the category of aromatic cyclic compounds.

As a method of synthesizing a cyclic poly (phenylene ether ether ketone), there is reported, for example, a method in which a linear poly (phenylene ether ether ketone) oligomer having a hydroxyl group at both terminals and a linear poly (phenylene ether ether ketone) oligomer having a fluorine group at both terminals are reacted as shown in the following reaction formula (for example, see Non-patent Document 1).

In this method, since long-chain oligomers are used as starting materials, the resulting poly (phenylene ether ether ketone) mixture is composed of cyclic poly (phenylene ether ether ketone) having a repeating number (m) of 3 and/or 6; therefore, this method can yield only a cyclic poly (phenylene ether ether ketone) having a melting point higher than 270° C. More specifically, it is described that the cyclic poly (phenylene ether ether ketone)s obtained from these linear oligomers shown in the above reaction formula (an oligomer having a hydroxyl group at both terminals, which is constituted by 4 benzene ring component units; and an oligomer having a fluorine group at both terminals, which is constituted by 5 benzene ring component units) are composed of only a cyclic trimer (m=3) and cyclic hexamer (m=6), which are cyclic poly (phenylene ether ether ketone)s having a melting point of 366° C. and 324° C., respectively. Further, Non-patent Document 1 also offers descriptions regarding the synthesis of a poly (phenylene ether ether ketone) by ring-opening polymerization of a cyclic poly (phenylene ether ether ketone); however, the cyclic poly (phenylene ether ether ketone) used therein is the one having a high melting point obtained in the above-described method. Moreover, the ring-opening polymerization is performed only in a temperature range of not lower than 340° C., that is, a temperature range which is not lower than the melting point of the poly (phenylene ether ether ketone), and there is no description at all with regard to ring-opening polymerization at a temperature not lower than the melting point of the poly (phenylene ether ether ketone).

Further, the same authors also discloses a method of producing a cyclic poly (phenylene ether ether ketone) by reacting a linear poly (phenylene ether ether ketone) oligomer having a hydroxyl group at both terminals with 4,4'-difluorobenzophenone as shown in the following reaction formula (for example, see Non-patent Document 2).

[Formula 2]

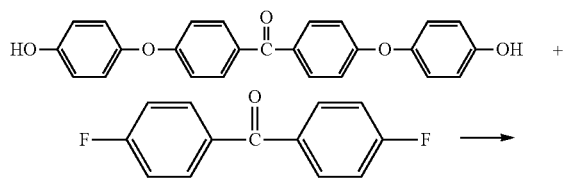

[Formula 1]

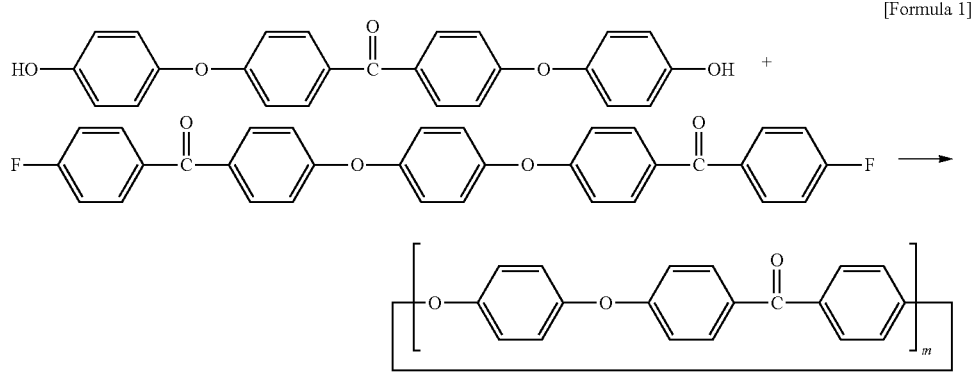

m = 3 or 6

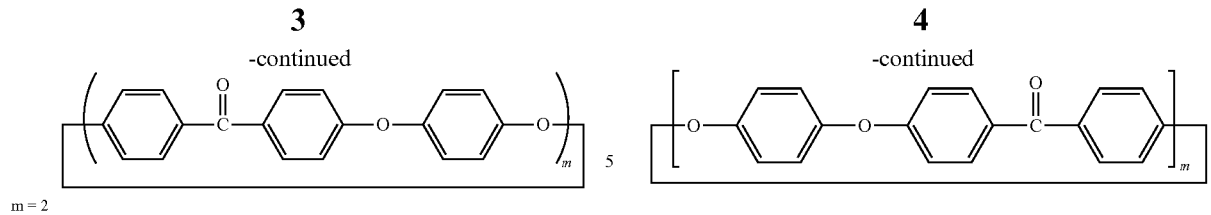

m = 2

It is described that the cyclic poly (phenylene ether ether ketone) obtained by this method is a mononuclear compound of a cyclic dimer (m=2) and has a melting point of not lower than 440° C. In this manner, the use of a linear poly (phenylene ether ether ketone) oligomer as a material for synthesizing a cyclic poly (phenylene ether ether ketone) can be considered as a significant method for the purpose of obtaining a cyclic poly (phenylene ether ether ketone) having a desired repeating number (m) in a high purity; however, by this method, it is difficult to produce the cyclic poly (phenylene ether ether ketone) composition of the present invention, which is characterized by being a mixture composed of cyclic poly (phenylene ether ether ketone)s having different repeating numbers (m) and having a melting point of not higher than 270° C. Further, in the synthesis of a cyclic poly (phenylene ether ether ketone) according to Non-patent Documents 1 and 2, since the reaction is performed under pseudo-high-dilution conditions, although the selectivity for the generation of cyclic poly (phenylene ether ether ketone) is high, an ultra-dilute condition must be maintained, so that the reaction requires an extremely long time. In addition, it is also required to perform the step of separately preparing the oligomer having a hydroxyl group at both terminals and the oligomer having a fluorine group at both terminals that are used as the materials for the synthesis of cyclic poly (phenylene ether ether ketone). Therefore, it is difficult to say that the methods according to Non-patent Documents 1 and 2 are industrially applicable production methods of a cyclic poly (phenylene ether ether ketone).

Further, there is also reported a method using an aromatic imine compound as a starting material for producing a cyclic poly (phenylene ether ether ketone) (for example, see Non-patent Document 3). Non-patent Document 3 discloses a method in which a cyclic poly (phenylene ether ether ketimine) is prepared from N-phenyl(4,4'-difluorodiphenyl) ketimine and hydroquinone as shown in the following reaction formula and the resulting cyclic poly (phenylene ether ether ketimine) is then hydrolyzed in an acidic condition to obtain a cyclic poly (phenylene ether ether ketone).

[Formula 3]

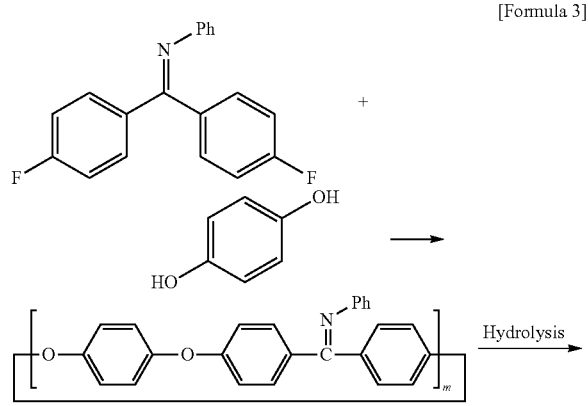

Since an aromatic ketimine compound generally has a low reactivity as compared to the corresponding aromatic ketone compound and the reaction is performed in an ultra-dilute condition, even after the completion of the synthesis reaction of the cyclic poly (phenylene ether ether ketimine), a low-molecular-weight linear oligomer, which is difficult to be separated from the cyclic poly (phenylene ether ether ketimine), remains. Therefore, this method can yield only a low-purity cyclic poly (phenylene ether ether ketone) containing a large amount of impurities. In addition, in order to produce a cyclic poly (phenylene ether ether ketone) by this method, it is indispensable to perform multiple complicated reaction steps, including at least the steps of preparing an aromatic ketimine compound used as a starting material; preparing and purifying a cyclic poly (phenylene ether ether ketimine); and preparing and purifying a cyclic poly (phenylene ether ether ketone) by hydrolyzing the thus obtained cyclic poly (phenylene ether ether ketimine). Therefore, it is difficult to say that this method is an industrially applicable production method of a cyclic poly (phenylene ether ether ketone). Furthermore, although there is no description in Non-patent Document 3 with regard to the melting point of the resulting cyclic poly (phenylene ether ether ketone), since it contains a large amount of linear poly (phenylene ether ether ketone) having a high melting point as an impurity, it is believed that the cyclic poly (phenylene ether ether ketone) obtained by this method has, unlike the one according to the present invention, a high melting point. Moreover, Non-patent Document 3 offers no description at all with regard to ring-opening polymerization of the cyclic poly (phenylene ether ether ketone) obtained by this method.

Further, there is also disclosed a method of producing a cyclic poly (phenylene ether ether ketone) using a phenylene ether oligomer as a starting material (for example, see Patent Document 1).

[Formula 4]

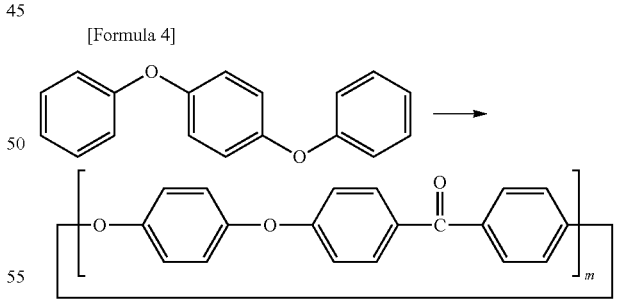

In Patent Document 1, it is described that a cyclic poly (phenylene ether ether ketone) can be prepared in a single step by a reaction of 1,4-diphenoxybenzene in the presence of a Lewis acid. Synthesis methods of poly (phenylene ether ketone)-type compounds can be generally classified into two types: synthesis methods based on ether bond formation by aromatic nucleophilic substitution reaction and synthesis methods based on ketone bond formation by aromatic electrophilic substitution reaction, and the route of the cyclic poly (phenylene ether ether ketone) synthesis according to Patent Document 1 is included in the latter type. One of the problems of using an aromatic electrophilic substitution reaction for the synthesis of a poly (phenylene ether ether ketone) is that the regioselectivity of the reaction is low. Therefore, the cyclic poly (phenylene ether ether ketone) obtained by the method described in Patent Document 1, too, is speculated to have a low purity, containing ortho-form and meta-form in addition to the desired para-form. Moreover, Patent Document 1 offers no description at all with regard to the melting point of the resulting cyclic poly (phenylene ether ether ketone).

PATENT DOCUMENTS

Patent Document 1: CN 101519399 A

NON-PATENT DOCUMENTS

Non-patent Document 1: Macromolecules 1996, 29, 5502
Non-patent Document 2: Macromol. Chem. Phys. 1996, 197, 4069
Non-patent Document 3: Polymer Bulletin 1999, 42, 245

SUMMARY OF THE INVENTION

The present invention provides a novel cyclic poly (phenylene ether ether ketone) composition in which the problems of those cyclic poly (phenylene ether ether ketone)s obtained by the above-described prior arts, that is, high melting point and poor processability, are solved. More particularly, the present invention provides a cyclic poly (phenylene ether ether ketone) composition comprising a cyclic poly (phenylene ether ether ketone), which has a superior property, that is, a low melting point, and can be synthesized by a simple method.

Embodiments of the present invention include as follows.
1. A cyclic poly (phenylene ether ether ketone) composition, which comprises not less than 60% by weight of a cyclic poly (phenylene ether ether ketone) represented by the following Formula (I), the cyclic poly (phenylene ether ether ketone) being a mixture of cyclic poly (phenylene ether ether ketone)s having different repeating numbers (m) and the composition having a melting point of not higher than 270° C.:

[Formula 5]

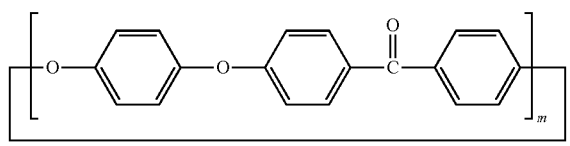

(wherein, m represents an integer of 2 to 40).
2. The cyclic poly (phenylene ether ether ketone) composition according to 1, wherein the cyclic poly (phenylene ether ether ketone) is a mixture composed of cyclic poly (phenylene ether ether ketone)s having at least 3 different integers (m).
3. The cyclic poly (phenylene ether ether ketone) composition according to 1, wherein the cyclic poly (phenylene ether ether ketone) is a mixture composed of cyclic poly (phenylene ether ether ketone)s having at least 3 consecutive different integers (m).
4. The cyclic poly (phenylene ether ether ketone) composition according to 1, wherein the composition has a reduced viscosity of not higher than 0.1 dL/g, the reduced viscosity being measured in sulfuric acid at 25° C.

5. A method of producing a poly (phenylene ether ether ketone), which is wherein the cyclic poly (phenylene ether ether ketone) composition according to 1 is subjected to thermal ring-opening polymerization.
6. The method of producing a poly (phenylene ether ether ketone) according to 5, wherein the thermal ring-opening polymerization is performed at a temperature not higher than the melting point of the resulting poly (phenylene ether ether ketone).
7. The method of producing a poly (phenylene ether ether ketone) according to 5, wherein the thermal ring-opening polymerization is performed in the presence or absence of a catalyst.
8. The method of producing a poly (phenylene ether ether ketone) according to 7, wherein the catalyst is an anionic polymerization initiator.
9. A method of producing the cyclic poly (phenylene ether ether ketone) composition according to 1, wherein when a mixture (M1) comprising at least a dihalogenated aromatic ketone compound, dihydroxy aromatic compound, base (A) and organic polar solvent is allowed to react by heating to produce the cyclic poly (phenylene ether ether ketone) composition, the organic polar solvent is used in an amount of not less than 1.20 L with respect to 1.0 mol of benzene ring component in the mixture (M1).
10. A method of producing the cyclic poly (phenylene ether ether ketone) composition according to 1, wherein when a mixture (M2) comprising at least a linear poly (phenylene ether ether ketone) represented by the following Formula (II):

[Formula 6]

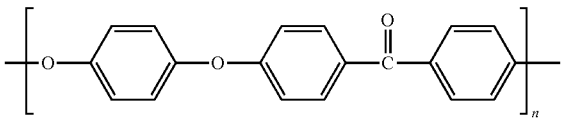

a dihalogenated aromatic ketone compound, a dihydroxy aromatic compound, a base (A) and an organic polar solvent is allowed to react by heating to produce the cyclic poly (phenylene ether ether ketone) composition, the organic polar solvent is used in an amount of not less than 1.20 L with respect to 1.0 mol of benzene ring component in the mixture (M2).
11. The method of producing the cyclic poly (phenylene ether ether ketone) composition according to 9, wherein the dihydroxy aromatic compound is hydroquinone.
12. A method of producing the cyclic poly (phenylene ether ether ketone) composition according to 1, wherein a mixture (M3) comprising at least a linear poly (phenylene ether ether ketone) represented by the following Formula (II):

Formula 7]

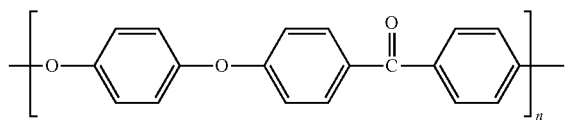

a basic compound (B) and an organic polar solvent is allowed to react by heating.
13. The method of producing the cyclic poly (phenylene ether ether ketone) composition according to 12, wherein the mixture (M3) further contains water.

14. The method of producing the cyclic poly (phenylene ether ether ketone) composition according to 12, wherein the basic compound (B) contained in the mixture (M3) is an alkali metal halide.

15. The method of producing the cyclic poly (phenylene ether ether ketone) composition according to 12, wherein the basic compound (B) contained in the mixture (M3) is an alkali metal carbonate and/or alkali metal bicarbonate.

According to an aspect of the present invention, a novel cyclic poly (phenylene ether ether ketone) composition comprising not less than 60% by weight of a cyclic poly (phenylene ether ether ketone), which is characterized by having a low melting point, can be provided. By this, the problems of those cyclic poly (phenylene ether ether ketone)s obtained by prior arts, that is, high melting point and poor processability, can be solved.

DETAILED DESCRIPTION OF THE INVENTION

The present invention will now be described in more detail.
(1) Cyclic Poly (Phenylene Ether Ether Ketone)

The cyclic poly (phenylene ether ether ketone) is a cyclic compound represented by the following Formula (I), which has p-phenylene ketone and p-phenylene ether as repeating structural unit.

[Formula 8]

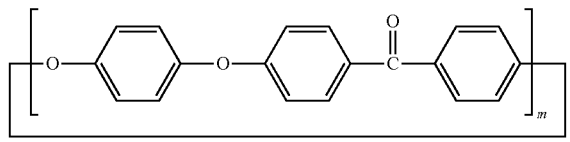

In the Formula (I), the repeating number (m) is, for example, in the range of 2 to 40, preferably 2 to 20, more preferably 2 to 15, particularly preferably 2 to 10. The melting point of the cyclic poly (phenylene ether ether ketone) tends to be high when the repeating number (m) is large; therefore, from the standpoint of melting the cyclic poly (phenylene ether ether ketone) at a low temperature, it is preferred that the repeating number (m) be set in the above-described range.

Further, the cyclic poly (phenylene ether ether ketone) represented by the Formula (I) is preferably a mixture composed of cyclic poly (phenylene ether ether ketone)s having different repeating numbers (m), more preferably at least 3 different repeating numbers (m), still more preferably at least 4 different repeating numbers (m), particularly preferably at least 5 different repeating numbers (m). Further, it is particularly preferred that these repeating numbers (m) be consecutive. As compared to a single compound having a single repeating number (m), a mixture composed of cyclic poly (phenylene ether ether ketone)s having different repeating numbers (m) tends to have a lower melting point. Also, as compared to a cyclic poly (phenylene ether ether ketone) mixture composed of cyclic poly (phenylene ether ether ketone)s having 2 different repeating numbers (m), the melting point of a mixture composed of cyclic poly (phenylene ether ether ketone)s having 3 or more different repeating numbers (m) tends to be even lower. Moreover, as compared to a mixture composed of cyclic poly (phenylene ether ether ketone)s having non-consecutive repeating numbers (m), a mixture composed of cyclic poly (phenylene ether ether ketone)s having consecutive repeating numbers (m) tends to have a further lower melting point. Here, the components of such cyclic poly (phenylene ether ether ketone)s having different repeating numbers (m) can be separated and analyzed by high-performance liquid chromatography. In addition, the composition of such cyclic poly (phenylene ether ether ketone)s, that is, the weight ratio of each cyclic poly (phenylene ether ether ketone) having the respective repeating number (m), can be calculated from the peak area ratio thereof obtained by high-performance liquid chromatography.

Further, the cyclic poly (phenylene ether ether ketone) composition is characterized by having a melting point of not higher than 270° C., which is considerably lower than that of the corresponding linear poly (phenylene ether ether ketone). The melting point of the cyclic poly (phenylene ether ether ketone) composition is, for example, preferably not higher than 250° C., more preferably not higher than 230° C. The lower the melting point of the cyclic poly (phenylene ether ether ketone) composition, the lower the processing temperature thereof can be and the lower the processing temperature can be set when producing a polymer having a high polymerization degree using the cyclic poly (phenylene ether ether ketone) as a poly (phenylene ether ether ketone) prepolymer; therefore, a lower melting point is advantageous from the viewpoint that the energy required for processing can be reduced. Here, the melting point of the cyclic poly (phenylene ether ether ketone) composition can be determined by measuring the endothermic peak temperature using a differential scanning calorimeter.

Further, the cyclic poly (phenylene ether ether ketone) composition comprises a cyclic poly (phenylene ether ether ketone) in an amount of not less than 60% by weight, preferably not less than 65%, more preferably not less than 70% by weight, still more preferably not less than 75% by weight. Examples of impurity component in the cyclic poly (phenylene ether ether ketone) composition, that is, a component other than the cyclic poly (phenylene ether ether ketone), mainly include linear poly (phenylene ether ether ketone)s. A linear poly (phenylene ether ether ketone) has a high melting point; therefore, when the weight ratio thereof is high, the melting point of the cyclic poly (phenylene ether ether ketone) composition tends to be high. Therefore, also from the viewpoints that the melting point of the cyclic poly (phenylene ether ether ketone) composition tends to be made low and that a poly (phenylene ether ether ketone) having a sufficiently high polymerization degree can be obtained when the cyclic poly (phenylene ether ether ketone) composition is used as a poly (phenylene ether ether ketone) prepolymer, it is preferred that the weight ratio of the cyclic poly (phenylene ether ether ketone) contained in the cyclic poly (phenylene ether ether ketone) composition be in the above-described range.

The reduced viscosity ($\eta$) of the cyclic poly (phenylene ether ether ketone) composition which has the above-described characteristics is, for example, preferably not higher than 0.1 dL/g, more preferably not higher than 0.09 dL/g, still more preferably not higher than 0.08 dL/g. It is noted here that, in the present invention, the reduced viscosity refers to, unless otherwise specified, a value measured by an Ostwald viscosimeter at 25° C. for a concentrated sulfuric acid solution having a concentration of 0.1 g/dL (the weight of cyclic poly (phenylene ether ether ketone) composition or linear poly (phenylene ether ether ketone)/the volume of 98%-by-weight concentrated sulfuric acid) immediately after the dissolution in order to minimize the effect of sulfonation. Further, the reduced viscosity was calculated using the following equation:

$$\eta = \{(t/t0) - 1\}/C$$

(wherein, t represents the transit time of the sample solution in seconds; t0 represents the transit time of the solvent (98%-by-weight concentrated sulfuric acid); and C represents the concentration of the solution).

Next, materials to be used in a preferred method of producing the cyclic poly (phenylene ether ether ketone) composition of the present invention will be described.

(2) Dihalogenated Aromatic Ketone Compound

The dihalogenated aromatic ketone compound used in the present invention is an aromatic ketone compound represented by the following Formula (III):

[Formula 9]

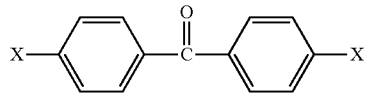

(III)

In the Formula (III), X represents a halogeno group selected from fluorine, chlorine, bromine, iodine, astatine and the like, and the two halogeno groups may be the same or different. Specific examples of such dihalogenated aromatic ketone compound include 4,4'-difluorobenzophenone, 4,4'-dichlorobenzophenone, 4,4'-dibromobenzophenone, 4,4'-diiodobenzophenone, 4-fluoro-4'-chlorobenzophenone, 4-fluoro-4'-bromobenzophenone, 4-fluoro-4'-iodobenzophenone, 4-chloro-4'-bromobenzophenone, 4-chloro-4'-iodobenzophenone and 4-bromo-4'-iodobenzophenone. Among these, 4,4'-difluorobenzophenone is preferred from the standpoint of the reactivity and 4,4'-dichlorobenzophenone is preferred from the standpoint of the economic efficiency, and a particularly preferred specific example is 4,4'-difluorobenzophenone. These dihalogenated aromatic ketone compounds may be used individually, or two or more thereof may be used as a mixture.

(3) Base (A)

Examples of the base (A) used in the production of the cyclic poly (phenylene ether ether ketone) composition according to the present invention include alkali metal carbonates such as lithium carbonate, sodium carbonate, potassium carbonate, rubidium carbonate and cesium carbonate; alkaline earth metal carbonates such as calcium carbonate, strontium carbonate and barium carbonate; alkali metal bicarbonates such as lithium bicarbonate, sodium bicarbonate, potassium bicarbonate, rubidium bicarbonate and cesium bicarbonate; alkaline earth metal bicarbonates such as calcium bicarbonate, strontium bicarbonate and barium bicarbonate; alkali metal hydroxides such as lithium hydroxide, sodium hydroxide, potassium hydroxide, rubidium hydroxide and cesium hydroxide; and alkaline earth metal hydroxides such as calcium hydroxide, strontium hydroxide and barium hydroxide. Among these, from the standpoints of the ease of handling and reactivity, carbonates such as sodium carbonate and potassium carbonate and bicarbonates such as sodium bicarbonate and potassium bicarbonate are preferred. Sodium carbonate and potassium carbonate are more preferred and potassium carbonate is still more preferably used. These bases may be used individually, or two or more thereof may be used in combination without any problem. Further, these bases (A) are preferably used in the form of an anhydride; however, they may also be used in the form of a hydrate or as an aqueous mixture. It is noted here that the term "aqueous mixture" used herein refers to an aqueous solution, a mixture of an aqueous solution and a solid component(s), or a mixture of water and a solid component(s).

(4) Dihydroxy Aromatic Compound

The dihydroxy aromatic compound used in a preferred method of producing the cyclic poly (phenylene ether ether ketone) composition according to the present invention is an aromatic compound represented by the following Formula (IV):

[Formula 10]

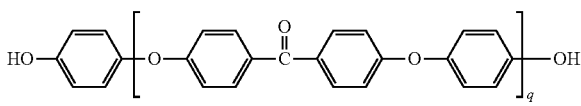

(IV)

In the Formula (IV), the repeating number (q) is not particularly restricted, and a preferred specific example of the dihydroxy aromatic compound is hydroquinone in which q is 0. Further, the upper limit of the repeating number (q) in the Formula (IV) is also not particularly restricted, and preferred examples of the dihydroxy aromatic compound include those in which q is 2 or smaller. These dihydroxy aromatic compounds may be used individually, or two or more thereof may be used as a mixture.

The amount of the dihydroxy aromatic compound to be used is preferably in the range of 0.8 to 1.2 mol, more preferably 0.9 to 1.1 mol, still more preferably 0.95 to 1.05 mol, particularly preferably 0.98 to 1.03 mol. It is preferred that the dihydroxy aromatic compound be used in an amount in the above-described range since the decomposition reaction of the resulting cyclic poly (phenylene ether ether ketone) can be thereby inhibited and the generation of a linear poly (phenylene ether ether ketone), which is difficult to be separated from cyclic poly (phenylene ether ether ketone), tends to be suppressed.

(5) Organic Polar Solvent

The organic polar solvent used in the method of producing the cyclic poly (phenylene ether ether ketone) composition according to the present invention is not particularly restricted as long as it does not substantially inhibit the reaction or cause undesirable side reactions such as decomposition of the resulting cyclic poly (phenylene ether ether ketone). Specific examples of such organic polar solvent include nitrogen-containing polar solvents such as N-methyl-2-pyrrolidone (NMP), N-methylcaprolactam, N,N-dimethylformamide (DMF), N,N-dimethylacetamide (DMAc), 1,3-dimethyl-2-imidazolidinone (DMI), hexamethylphosphoramide and tetramethylurea; sulfoxide/sulfone-based solvents such as dimethyl sulfoxide (DMSO), dimethyl sulfone, diphenyl sulfone and sulfolane; nitrile-based solvents such as benzonitrile; diaryl ethers such as diphenyl ether; ketones such as benzophenone and acetophenone; and mixtures thereof. All of these organic polar solvents have high reaction stability and are, therefore, suitably used; however, preferred thereamong are N-methyl-2-pyrrolidone and dimethyl sulfoxide and N-methyl-2-pyrrolidone is particularly preferably used. These organic polar solvents are said to be preferable since they have excellent stability in a high temperature range, as well as from the standpoint of the availability.

(6) Linear Poly (Phenylene Ether Ether Ketone)

The linear poly (phenylene ether ether ketone) in the present invention is a linear compound represented by the following Formula (II), which has p-phenylene ketone and p-phenylene ether as repeating structural unit.

[Formula 11]

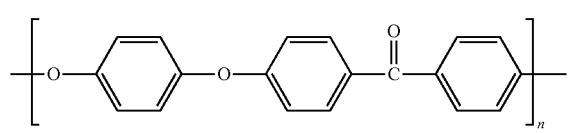

(II)

In the Formula (II), the repeating number (n) is not particularly restricted; however, it is, for example, in the range of 10 to 10,000, preferably 20 to 5,000, more preferably 30 to 1,000.

Further, the reduced viscosity (η) of the linear poly (phenylene ether ether ketone) in the present invention is not particularly restricted; however, in general, it is usually in the range of, for example, 0.1 to 2.5 dL/g, preferably 0.2 to 2.0 dL/g, more preferably 0.3 to 1.8 dL/g. Generally, the lower the reduced viscosity of a linear poly (phenylene ether ether ketone), that is, the lower the molecular weight of a linear poly (phenylene ether ether ketone), the higher the solubility thereof to an organic polar solvent becomes; therefore, a lower viscosity is advantageous in that the time required for the reaction can be reduced; however, any linear poly (phenylene ether ether ketone) can be used with no substantial problem as long as the reduced viscosity thereof is in the above-described range.

The method of producing such linear poly (phenylene ether ether ketone) is not particularly restricted and any production method may be employed. For example, as represented by JP S54-90296A and JP S59-93724A, such linear poly (phenylene ether ether ketone) can be produced by performing a polycondensation reaction between an aromatic dihalogen compound and diphenol in the presence of an alkali salt. Moreover, molded articles, molding wastes, waste plastics, off-spec products and the like, in which a poly (phenylene ether ether ketone) produced by these methods are used, can be widely employed as well.

Generally, production of a cyclic compound is based on competitive reactions of cyclic compound generation and linear compound generation; therefore, in a method for producing a cyclic poly (phenylene ether ether ketone), in addition to the desired cyclic poly (phenylene ether ether ketone), a linear poly (phenylene ether ether ketone) is generated as a by-product in no small amount. In the present invention, such by-product linear poly (phenylene ether ether ketone) can also be utilized without any problem; therefore, a method utilizing such linear poly (phenylene ether ether ketone), which is obtained by separating a cyclic poly (phenylene ether ether ketone) from a mixture containing the cyclic poly (phenylene ether ether ketone) and linear poly (phenylene ether ether ketone) generated by the later-described preferred production method of cyclic poly (phenylene ether ether ketone), is said to be a particularly preferred method. Conventionally, those linear compounds and linear poly (phenylene ether ether ketone)s that are generated as by-product during the production of a cyclic compound or cyclic poly (phenylene ether ether ketone) have been considered to be of no utility value and thus disposed. Therefore, in the production of a cyclic compound, there are problems in that a large amount of waste is generated due to such by-product linear compounds and that the material monomer-based yield is low. In the present invention, such by-product linear poly (phenylene ether ether ketone)s can be utilized as a starting material, and this is of great significance from the standpoint of enabling a considerable decrease in the waste amount and a drastic improvement in the material monomer-based yield.

Here, the form of the linear poly (phenylene ether ether ketone) is not particularly restricted, and it may be in the form of dry powder, granule, particle or pellet. It is also possible to use the linear poly (phenylene ether ether ketone) in a form containing an organic solvent, which is the reaction solvent, or in a form containing a third component which does not substantially inhibit the reaction. Examples of such third component include inorganic fillers and the linear poly (phenylene ether ether ketone) may also be used in the form of a resin composition containing an inorganic filler.

(7) Basic Compound (B)

As the basic compound (B), a wide range of known inorganic bases and organic bases can be used. Examples of the inorganic bases include carbonates of alkali metals and alkaline earth metals, such as lithium carbonate, sodium carbonate, potassium carbonate, rubidium carbonate, cesium carbonate, calcium carbonate, strontium carbonate and barium carbonate; bicarbonates of alkali metals and alkaline earth metals, such as lithium bicarbonate, sodium bicarbonate, potassium bicarbonate, rubidium bicarbonate, cesium bicarbonate, calcium bicarbonate, strontium bicarbonate and barium bicarbonate; hydroxides of alkali metals and alkaline earth metals, such as lithium hydroxide, sodium hydroxide, potassium hydroxide, rubidium hydroxide, cesium hydroxide, calcium hydroxide, strontium hydroxide and barium hydroxide; phosphates of alkali metals and alkaline earth metals, such as lithium phosphate, sodium phosphate, potassium phosphate, rubidium phosphate, cesium phosphate, calcium phosphate, strontium phosphate and barium phosphate; halides of alkali metals and alkaline earth metals, such as lithium fluoride, sodium fluoride, potassium fluoride, rubidium fluoride, cesium fluoride, calcium fluoride, strontium fluoride, barium fluoride, lithium chloride, sodium chloride, potassium chloride, rubidium chloride, cesium chloride, calcium chloride, strontium chloride, barium chloride, lithium bromide, sodium bromide, potassium bromide, rubidium bromide, cesium bromide, calcium bromide, strontium bromide, barium bromide, lithium iodide, sodium iodide, potassium iodide, rubidium iodide, cesium iodide, calcium iodide, strontium iodide and barium iodide; hydrides of alkali metals and alkaline earth metals, such as lithium hydride, sodium hydride, potassium hydride, rubidium hydride, cesium hydride, calcium hydride, strontium hydride and barium hydride; alkali metals; and ammonia. Further, specific examples of the organic bases include alkoxides and phenoxides of alkali metals, such as sodium methoxide, potassium methoxide, sodium ethoxide, potassium ethoxide, sodium tert-butoxide and potassium tert-butoxide; alkali metal acetates such as lithium acetate, sodium acetate, potassium acetate, rubidium acetate and cesium acetate; primary amines such as methylamines, ethylamines and butylamines; secondary amines such as dimethylamines and diethylamines; tertiary amines such as triethylamines and tributylamines; and organic amine compounds such as anilines and pyridines. Among these, from the standpoint of the reactivity, alkali metal halides such as lithium fluoride, sodium fluoride, potassium fluoride, rubidium fluoride, cesium fluoride, lithium chloride, sodium chloride, potassium chloride, rubidium chloride, cesium chloride, lithium bromide, sodium bromide, potassium bromide, rubidium bromide, cesium bromide, lithium iodide, sodium iodide, potassium iodide, rubidium iodide and cesium iodide are preferred, and specific examples of more preferred alkali metal halides include alkali metal fluorides such as lithium fluoride, sodium fluoride, potassium fluoride, rubidium fluoride and cesium fluoride. These inorganic and organic bases may be used individually, or two or more thereof may be used in combination without any problem.

Further, other preferred specific examples include carbonates of alkali metals and alkaline earth metals, such as lithium carbonate, sodium carbonate, potassium carbonate, rubidium carbonate, cesium carbonate, calcium carbonate, strontium carbonate and barium carbonate; and bicarbonates of alkali metals and alkaline earth metals, such as lithium bicarbonate, sodium bicarbonate, potassium bicarbonate, rubidium bicarbonate, cesium bicarbonate, calcium bicarbonate, strontium bicarbonate and barium bicarbonate. Among these, sodium carbonate and potassium carbonate are more preferred, and a particularly preferred specific example is potassium carbonate. These may also be used individually, or two or more thereof may be used in combination without any problem.

(8) Method of Producing Cyclic Poly (Phenylene Ether Ether Ketone) Composition

As the method of producing a cyclic poly (phenylene ether ether ketone) composition, any method may be employed as long as a cyclic poly (phenylene ether ether ketone) composition having the above-described characteristics can be produced; however, it is strongly desired to employ, as a preferred method, a production method (a) in which a mixture (M1) containing at least a dihalogenated aromatic ketone compound, dihydroxy aromatic compound, base (A) and organic polar solvent is allowed to react by heating; a production method (b) in which a mixture (M2) containing at least a linear poly (phenylene ether ether ketone), dihalogenated aromatic ketone compound, dihydroxy aromatic compound, base (A) and organic polar solvent is allowed to react by heating; or a production method (c) in which a mixture (M3) containing at least a linear poly (phenylene ether ether ketone), basic compound (B) and organic polar solvent is allowed to react by heating. These preferred methods of producing a cyclic poly (phenylene ether ether ketone) will now be described in detail.

(8)-1. Production Methods (a) and (b)

Examples of preferred methods of producing a cyclic poly (phenylene ether ether ketone) include a method (a) in which a mixture (M1) containing at least a dihalogenated aromatic ketone compound, dihydroxy aromatic compound, base (A) and organic polar solvent is allowed to react by heating; and a method (b) in which a mixture (M2) containing at least a linear poly (phenylene ether ether ketone), dihalogenated aromatic ketone compound, dihydroxy aromatic compound, base (A) and organic polar solvent is allowed to react by heating.

When producing a cyclic poly (phenylene ether ether ketone) composition by these preferred methods, the mixture contains the organic polar solvent in an amount of preferably not less than 1.20 L, more preferably not less than 1.30 L, still more preferably not less than 1.50 L, particularly preferably not less than 2.0 L, with respect to 1.0 mol of the benzene ring component in the respective mixture (M1) or (M2). Further, the upper limit of the amount of the organic polar solvent in each mixture is not particularly restricted; however, it is preferably not greater than 100 L, more preferably not greater than 50 L, still more preferably not greater than 20 L, particularly preferably not greater than 10 L, with respect to 1.0 mol of the benzene ring component in the mixture. When the organic polar solvent is used in a large amount, the selectivity for the cyclic poly (phenylene ether ether ketone) generation tends to be improved; however, when the amount is excessive, the amount of generated cyclic poly (phenylene ether ether ketone) per unit volume of reaction vessel tends to be decreased and the time required for the reaction tends to be prolonged. Therefore, from the viewpoint of satisfying both the production selectivity and productivity of cyclic poly (phenylene ether ether ketone), it is preferred that the organic polar solvent be used in an amount in the above-described range. Here, the amount of the organic polar solvent is based on the volume thereof at normal temperature and pressure, and the amount of the organic polar solvent used in each reaction mixture is an amount obtained by subtracting the amount of the organic polar solvent removed to outside the reaction system by a dehydration operation or the like from the amount of the organic polar solvent introduced to the reaction system. Further, the term "benzene ring component in the mixture" used herein refers to a benzene ring component contained in a starting material which can be a constituent of a cyclic poly (phenylene ether ether ketone) through a reaction, and "the number of moles" of the benzene ring component in such starting material represents "the number of benzene rings constituting a compound". For instance, 1 mol of 4,4'-difluorobenzophenone and 1 mol of hydroquinone are said to contain 2 mol of benzene ring component and 1 mol of benzene ring component, respectively, and a mixture containing 1 mol of 4,4'-difluorobenzophenone and 1 mol of hydroquinone is thus calculated to contain 3 mol of benzene ring component. Further, in the production method (b), since the linear poly (phenylene ether ether ketone) used in the reaction is also a starting material which can be a constituent of the resulting cyclic poly (phenylene ether ether ketone), it is required to take into consideration the number of moles of the benzene ring component in the linear poly (phenylene ether ether ketone) as well. It is noted there that the linear poly (phenylene ether ether ketone) and cyclic poly (phenylene ether ether ketone) are polymers containing 3 benzene rings in the respective repeating units. Therefore, "the number of moles" of benzene ring component contained in these linear poly (phenylene ether ether ketone) and cyclic poly (phenylene ether ether ketone) is "the number of repeating units of poly (phenylene ether ether ketone)×3". For example, one molecule of poly (phenylene ether ether ketone) having a polymerization degree of 100 is calculated to contain 300 mol of benzene ring component, not 1 mol. Moreover, those components which cannot be a constituent of a cyclic poly (phenylene ether ether ketone) through a reaction, such as toluene, are regarded to contain 0 mol of benzene ring component.

In the production methods (a) and (b) of a cyclic poly (phenylene ether ether ketone) composition, it is preferred that the base (A) be used in an amount equivalent to that of the dihydroxy aromatic compound based on the stoichiometric ratio. Specifically, for example, when the amount of a divalent base used, such as sodium carbonate or potassium carbonate, is defined as Y mol and the amount of a monovalent base used, such as sodium bicarbonate or potassium bicarbonate, is defined as Z mol, the base (A) is used in such an amount that (Y+2Z) is in the range of preferably 1.00 to 1.10 mol, more preferably 1.00 mol to 1.05 mol, still more preferably 1.00 mol to 1.03 mol, with respect to 1.0 mol of the dihydroxy aromatic compound used in the production of a cyclic poly (phenylene ether ether ketone) composition. When producing a cyclic poly (phenylene ether ether ketone) composition by the preferred production method (a) or (b), it is preferred that the base (A) be used in an amount in the preferred range since a metal salt of the dihydroxy aromatic compound can be sufficiently generated and the progress of undesirable reactions, such as decomposition reaction of the resulting cyclic poly (phenylene ether ether ketone) caused by a large excess base, can be inhibited as well.

Further, when producing a cyclic poly (phenylene ether ether ketone) composition by the production method (a) or (b), a metal salt of dihydroxy aromatic compound separately prepared from the dihydroxy aromatic compound and base (A) can also be used, and in this case, the above-described preferred base (A) can be added to supply an excess amount of base. This excess amount of the base (A) supplied is such an amount that (Y+2Z) is, for example, in the range of preferably 0 to 0.10 mol, more preferably 0 to 0.05 mol, still more preferably 0 to 0.03 mol, with respect to 1.0 mol of the dihydroxy aromatic compound used in the production of cyclic poly (phenylene ether ether ketone) composition. It is preferred that the excess amount of the base (A) be in such preferred range since the progress of an undesirable reaction, such as decomposition reaction of the resulting cyclic poly (phenylene ether ether ketone), can also be inhibited.

In the method (b) of producing a cyclic poly (phenylene ether ether ketone) composition where the mixture (M2) containing at least a linear poly (phenylene ether ether ketone), dihalogenated aromatic ketone compound, dihydroxy aromatic compound, base (A) and organic polar solvent is allowed to react by heating, the linear poly (phenylene ether ether ketone) may be used in any amount as long as it is contained in the reaction mixture at the beginning of the reaction, that is, at the stage where the degree of conversion of the dihalogenated aromatic ketone compound loaded to the reaction system is 0; however, based on the repeating unit represented by the following formula, which is the major structural unit of linear poly (phenylene ether ether ketone):

[Formula 12]

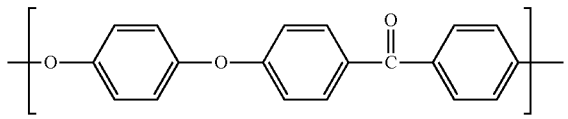

the amount of the linear poly (phenylene ether ether ketone) is in the range of preferably 0.1 to 30 mol of the repeating unit, more preferably 0.25 to 20 mol of the repeating unit, still more preferably 0.5 to 15 mol of the repeating unit, particularly preferably 1 to 10 mol of the repeating unit, with respect to 1 mol of the dihydroxy aromatic compound. When the amount of the linear poly (phenylene ether ether ketone) is in this preferred range, a cyclic poly (phenylene ether ether ketone) tends to be obtained in particularly high yield and the reaction tends to be able to progress in a short time.

The reaction temperature at which the mixture (M1) containing at least a dihalogenated aromatic ketone compound, dihydroxy aromatic compound, base (A) and organic polar solvent or the mixture (M2) containing at least a linear poly (phenylene ether ether ketone), dihalogenated aromatic ketone compound, dihydroxy aromatic compound, base (A) and organic polar solvent is allowed to react by heating cannot be uniquely prescribed since it varies depending on the types and amounts of the dihalogenated aromatic ketone compound, dihydroxy aromatic compound, base (A), organic polar solvent and linear poly (phenylene ether ether ketone) that are used in the reaction; however, the reaction temperature is, for example, in the range of usually 120 to 350° C., preferably 150 to 330° C., more preferably 200 to 320° C. Further, in the method (b) of producing a cyclic poly (phe-nylene ether ether ketone) composition, the reaction temperature is, for example, particularly preferably in the range of 250 to 300° C. In the above-described preferred temperature range, a higher reaction rate tends to be attained. Moreover, the reaction may be performed in a single step at a constant temperature or in multiple steps where the temperature is changed stepwise, or the reaction may be performed in such a manner that the temperature is changed continuously.

The reaction time cannot be generally prescribed since it depends on the types and amounts of the starting materials as well as the reaction temperature; however, it is preferably not shorter than 0.1 hour, more preferably not shorter than 0.5 hour, still more preferably not shorter than 1 hour. By performing the reaction for a period of not shorter than this preferred time, the amount of unreacted starting materials tends to be sufficiently reduced. Meanwhile, the upper limit of the reaction time is not particularly restricted; however, the reaction sufficiently progresses even within 40 hours, and the reaction may thus be performed for a period of preferably not longer than 10 hours, more preferably not longer than 6 hours.

When allowing the mixture (M1), which contains at least a dihalogenated aromatic ketone compound, dihydroxy aromatic compound, base (A) and organic polar solvent, or the mixture (M2) which contains at least a linear poly (phenylene ether ether ketone), dihalogenated aromatic ketone compound, dihydroxy aromatic compound, base (A) and organic polar solvent, to react by heating, in addition to the above-described indispensable components, a component which does not substantially inhibit the reaction and/or a component having an effect to accelerate the reaction may also be added to the mixture (M1) or (M2). In these preferred methods (a) and (b) of producing a cyclic poly (phenylene ether ether ketone) composition, the method of loading the above-described indispensable components is not particularly restricted; however, preferred examples of the production method (b) include a method in which a mixture containing at least a linear poly (phenylene ether ether ketone), dihydroxy aromatic ketone compound, base (A) and organic polar solvent is allowed to react by heating to obtain a reaction mixture to which a dihalogenated aromatic compound or a dihalogenated aromatic ketone compound and organic polar solvent is/are further added, and the resultant is then allowed to react by heating. Further, the method of performing the reaction is not particularly restricted; however, it is preferred that the reaction be performed with stirring. Moreover, in the method of producing a cyclic poly (phenylene ether ether ketone) composition according to the present invention, a variety of known polymerization techniques and reaction processes, such as those of batchwise type and continuous type, can be adopted. Furthermore, the atmosphere in which the production is carried out is desirably a non-oxidizing atmosphere. It is preferred that the production be carried out in an inert atmosphere such as nitrogen, helium or argon and, from the standpoints of the economic efficiency and ease of handling, the production is preferably carried out in a nitrogen atmosphere.

Further, in the above-described reaction, when a large amount of water is present in the reaction system, adverse effects, such as a decrease in the reaction rate and generation of a side reaction product which is difficult to be separated from cyclic poly (phenylene ether ether ketone), tend to be elicited. The amount of the water present in the system during the reaction is preferably not greater than 3.0% by weight, more preferably not greater than 1.0% by weight, still more preferably not greater than 0.5% by weight, particularly preferably not greater than 0.3% by weight. Accordingly, it is preferred that the amount of the water be controlled to be not greater than the above-described preferred range by performing, as required, an operation to remove the water generated when a hydrate or aqueous mixture is used as the base (A) or the water generated as a by-product in the reaction to outside the reaction system. It is noted here that the amount of the water present in the system is expressed as a weight ratio based on the total weight of the reaction mixture and can be measured by the Karl Fischer Method. The timing of such dehydration operation is not particularly restricted; however, it is preferably (i) after mixing the indispensable components in the production method (a) or (b), or (ii) after mixing the indispensable components other than dihalogenated aromatic ketone compound. Here, in cases where the dehydration operation is performed at the timing of (ii), a dihalogenated aromatic ketone compound, or a dihalogenated aromatic ketone compound and organic polar solvent, are added after the dehydration operation to produce a cyclic poly (phenylene ether ether ketone) composition. As the method of removing the water, any method can be employed as long as it can remove the water to outside the reaction system, and examples thereof include those methods utilizing dehydration by high-temperature heating or azeotropic distillation with an azeotropic solvent. Among such methods, from the standpoint of the dehydration efficiency, a method utilizing azeotropic distillation is preferred. Here, as the azeotropic solvent used in azeotropic distillation, any solvent may be used as long as it is an organic compound capable of forming an azeotropic mixture with water and the resulting azeotropic mixture has a boiling point lower than that of the organic polar solvent used in the reaction. Specific examples of such azeotropic solvent include hydrocarbon-based solvents such as hexane, cyclohexane, heptane, benzene, toluene and xylene and inert chlorinated aromatic compounds such as chlorobenzene and dichlorobenzene, and preferred thereamong are toluene and xylene. Further, the amount of the azeotropic solvent required for forming an azeotropic mixture with water cannot be generally prescribed since it varies depending on the amount of the water present in the system and the type of the solvent; however, it is preferred that the azeotropic solvent be used in an amount larger than the amount required for removing the water present in the reaction system as an azeotropic mixture. Specifically, the amount of the azeotropic solvent is preferably not less than 0.2 L, more preferably not less than 0.5 L, still more preferably not less than 1.0 L, with respect to 1.0 mol of the dihydroxy aromatic compound in the mixture. Further, the upper limit of the amount of the azeotropic solvent is not particularly restricted; however, it is preferably not greater than 20.0 L, more preferably not greater than 10.0 L, still more preferably not greater than 5.0 L, with respect to 1.0 mol of the dihydroxy aromatic compound in the mixture. When the azeotropic solvent is used in an excessive amount, since the polarity in the mixture is decreased, the efficiency of the reaction between the base and dihydroxy aromatic compound tends to be impaired. It is noted here that the amount of the azeotropic solvent is based on the volume thereof at normal temperature and pressure. Moreover, in cases where water is azeotropically distilled in accordance with the principles of a Dean-Stark apparatus, the amount of the azeotropic solvent in the reaction system can be maintained constant all the time; therefore, it is also possible to further reduce the amount of the azeotropic solvent used. The temperature at which the water is removed to outside the reaction system cannot be uniquely prescribed since the boiling point of the azeotropic mixture with water varies depending on the type of the azeotropic solvent; however, it is preferably not lower than the boiling point of the azeotropic mixture with water and not higher than the boiling point of the organic polar solvent used in the reaction. Specifically, for example, it is in the range of 60 to 170° C., preferably 80 to 170° C., more preferably 100 to 170° C., still more preferably 120 to 170° C. Here, the removal of water may be performed by any of a method in which the temperature is maintained constant in the above-described preferred temperature range, a method in which the temperature is increased stepwise and a method in which the temperature is changed continuously. Furthermore, a method in which the above-described azeotropic distillation is performed under reduced pressure is also preferred, and such azeotropic distillation under reduced pressure tends to be able to remove water more efficiently.

It is preferred that the above-described azeotropic solvent be removed from the system after the azeotropic distillation. The azeotropic solvent is preferably removed from the system after completion of the azeotropic distillation of water, and in cases where the dehydration operation is perform at the above-described timing of (ii), it is preferred that the azeotropic solvent be removed before adding a dihalogenated aromatic ketone compound or a dihalogenated aromatic ketone compound and organic polar solvent. When the azeotropic solvent remains in the system in a large amount, the polarity of the reaction system is reduced and the rate of the cyclic poly (phenylene ether ether ketone)-generating reaction tends to be decreased; therefore, it is desired to remove the residual azeotropic solvent. The amount of the azeotropic solvent remaining in the system during the cyclic poly (phenylene ether ether ketone)-generating reaction is preferably not greater than 20%, more preferably not greater than 10%, still more preferably not greater than 8%, particularly preferably not greater than 6%, with respect to the amount of the organic polar solvent used in the cyclic poly (phenylene ether ether ketone)-generating reaction. It is important that the removal of the azeotropic solvent be performed such that the residual amount thereof is not greater than the above-described preferred range. As the method of removing the azeotropic solvent, a method utilizing distillation is preferred, and an inert gas such as nitrogen, helium or argon may also be used as a carrier gas. Further, a method in which distillation is performed under reduced pressure is also preferred since the azeotropic solvent tends to be removed more efficiently. Moreover, the removal of the azeotropic solvent may be performed at any temperature as long as the azeotropic solvent can be removed from the reaction system, and specifically, for example, the removal of the azeotropic solvent is performed at a temperature of 60 to 170° C., preferably 100 to 170° C., more preferably 120 to 170° C., still more preferably 140 to 170° C. Here, the removal of the azeotropic solvent may be performed by any of a method in which the temperature is maintained constant in the above-described preferred temperature range, a method in which the temperature is increased stepwise and a method in which the temperature is changed continuously.

In these preferred methods (a) and (b) of producing a cyclic poly (phenylene ether ether ketone) composition, the yield of cyclic poly (phenylene ether ether ketone) mixture tends to be not lower than 1.0%, preferably not lower than 3.0%, more preferably not lower than 5.0%; therefore, these methods are said to be efficient in producing a cyclic poly (phenylene ether ether ketone) composition.

(8)-2. Production Method (c)

Another example of preferred method of producing a cyclic poly (phenylene ether ether ketone) composition is a method (c) in which a mixture (M3) containing at least a linear poly (phenylene ether ether ketone), basic compound (B) and organic polar solvent is allowed to react by heating.

When producing a cyclic poly (phenylene ether ether ketone) composition by this method, the amount of the organic polar solvent contained in the mixture (M3) is not particularly restricted; however, the mixture contains the organic polar solvent in an amount of preferably not less than 1.20 L, more preferably not less than 1.30 L, still more preferably not less than 1.50 L, particularly preferably not less than 2.0 L, with respect to 1.0 mol of the benzene ring component in the mixture. Further, the upper limit of the amount of the organic polar solvent in the mixture is also not particularly restricted; however, it is preferably not greater than 100 L, more preferably not greater than 50 L, still more preferably not greater than 20 L, particularly preferably not greater than 10 L, with respect to 1.0 mol of the benzene ring component in the mixture. When the organic polar solvent is used in a large amount, the selectivity for the cyclic poly (phenylene ether ether ketone) generation tends to be improved; however, when the amount is excessive, the amount of generated cyclic poly (phenylene ether ether ketone) per unit volume of reaction vessel tends to be decreased and the time required for the reaction tends to be prolonged. Therefore, from the viewpoint of satisfying both the production selectivity and productivity of cyclic poly (phenylene ether ether ketone), the above-described range can be exemplified as a preferred range of the amount of the organic polar solvent to be used. Here, the amount of the organic polar solvent is based on the volume thereof at normal temperature and pressure, and the amount of the organic polar solvent used in the reaction mixture is an amount obtained by subtracting the amount of the organic polar solvent removed to outside the reaction system by a dehydration operation or the like from the amount of the organic polar solvent introduced to the reaction system. Further, the term "benzene ring component in the mixture" used herein refers to a benzene ring component contained in a starting material which can be a constituent of a cyclic poly (phenylene ether ether ketone) through a reaction, and "the number of moles" of the benzene ring component in such starting material represents "the number of benzene rings constituting a compound".

In the method (c) of producing a cyclic poly (phenylene ether ether ketone) composition where the mixture (M3) containing at least a linear poly (phenylene ether ether ketone), basic compound (B) and organic polar solvent is allowed to react by heating, the amount of the basic component (B) used is not particularly restricted; however, based on the repeating unit represented by the following formula, which is the major structural unit of linear poly (phenylene ether ether ketone):

[Formula 13]

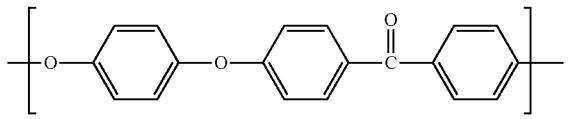

the amount of the basic component (B) is, for example, in the range of preferably 0.001 to 10 mol, more preferably 0.01 to 5 mol, still more preferably 0.05 to 5 mol, with respect to 1 mol of the repeating unit. In the method (c) of producing a cyclic poly (phenylene ether ether ketone) composition where the mixture (M3) containing at least a linear poly (phenylene ether ether ketone), basic compound (B) and organic polar solvent is allowed to react by heating, when the amount of the basic component (B) is in the above-described preferred range, a cyclic poly (phenylene ether ether ketone) tends to be obtained in particularly high yield and the reaction tends to be able to progress in a short time.

When allowing the mixture (M3) containing at least a linear poly (phenylene ether ether ketone), basic compound (B) and organic polar solvent to react by heating, in addition to the above-described indispensable components, water may also be added to the mixture (M3). In this case, the amount of the water is not particularly restricted; however, for example, it is in the range of preferably 0.01 to 100 mol, more preferably 0.1 to 50 mol, still more preferably 0.5 to 10 mol, with respect to 1.0 mol of the basic compound (B). When the amount of the added water is in the above-described preferred range, a cyclic poly (phenylene ether ether ketone) tends to be obtained in particularly high yield and the content ratio of the cyclic poly (phenylene ether ether ketone) in the resulting cyclic poly (phenylene ether ether ketone) composition tends to be thus high. Further, examples of the basic compound (B) preferably used in the method (c) of producing a cyclic poly (phenylene ether ether ketone) composition include alkali metal halides, alkali metal carbonates and alkali metal bicarbonates. The above-described effects can be attained with any of these preferable basic compounds (B) by adding water; however, these effects attained by addition of water tend to be exhibited more prominently when, among those preferably basic compounds, an alkali metal carbonate and/or an alkali metal bicarbonate is/are used as the basic compound (B). Therefore, in cases where a cyclic poly (phenylene ether ether ketone) composition is produced by the production method (c) using an alkali metal carbonate and/or an alkali metal bicarbonate as the basic compound (B), an addition of water to the reaction mixture (M3) can be exemplified as a more preferred embodiment.

The reaction temperature at which the mixture (M3) containing at least a linear poly (phenylene ether ether ketone), basic compound (B) and organic polar solvent is allowed to react by heating cannot be uniquely prescribed since it varies depending on the types and amounts of the basic compound (B), organic polar solvent and linear poly (phenylene ether ether ketone) that are used in the reaction; however, the reaction temperature is, for example, in the range of usually 120 to 350° C., preferably 150 to 330° C., more preferably 200 to 320° C. In this preferred temperature range, a higher reaction rate tends to be attained. Moreover, the reaction may be performed in a single step at a constant temperature or in multiple steps where the temperature is changed stepwise, or the reaction may be performed in such a manner that the temperature is changed continuously.

The reaction time cannot be generally prescribed since it depends on the types and amounts of the starting materials as well as the reaction temperature; however, it is preferably not shorter than 0.1 hour, more preferably not shorter than 0.5 hour, still more preferably not shorter than 1 hour. By performing the reaction for a period of not shorter than this preferred time, the amount of unreacted starting materials tends to be sufficiently reduced. Meanwhile, the upper limit of the reaction time is not particularly restricted; however, the reaction sufficiently progresses even within 40 hours, and the reaction may thus be performed for a period of preferably not longer than 10 hours, more preferably not longer than 6 hours.

When allowing the mixture (M3) containing at least a linear poly (phenylene ether ether ketone), basic compound (B) and organic polar solvent to react by heating, in addition to the above-described components, a component which does not substantially inhibit the reaction and/or a component having an effect to accelerate the reaction may also be added to the mixture (M3). Further, the method of performing the reaction is not particularly restricted; however, it is preferred that the reaction be performed with stirring. Moreover, in the method of producing a cyclic poly (phenylene ether ether ketone) composition according to the present invention, a variety of known polymerization techniques and reaction processes, such as those of batchwise type and continuous type, can be adopted. Furthermore, the atmosphere in which the production is carried out is desirably a non-oxidizing atmosphere. It is preferred that the production be carried out in an inert atmosphere such as nitrogen, helium or argon and, from the standpoints of the economic efficiency and ease of handling, the production is preferably carried out in a nitrogen atmosphere.

In the preferred method (c) of producing a cyclic poly (phenylene ether ether ketone) composition, the yield of cyclic poly (phenylene ether ether ketone) mixture tends to be not lower than 1.0%, preferably not lower than 3.0%, more preferably not lower than 5.0%; therefore, the method (c) is said to be an efficient production method of a cyclic poly (phenylene ether ether ketone) composition.

The representative reaction schemes of the above-described production methods (a), (b) and (c) of a cyclic poly (phenylene ether ether ketone) composition are shown below.

ether ether ketone), linear poly (phenylene ether ether ketone) and organic polar solvent, and in some cases, the reaction mixture also contains, for example, an unreacted starting material, by-product salt, water and/or azeotropic solvent as other components. The method of recovering a cyclic poly (phenylene ether ether ketone) from such reaction mixture is not particularly restricted, and an example thereof is one in which, after removing as required a part or majority of the organic polar solvent by distillation or the like, the resultant is brought into contact with a solvent under heating as required, which solvent has a low solubility for the poly (phenylene ether ether ketone) components and is miscible with the organic polar solvent and capable of dissolving the by-product salt, thereby the cyclic poly (phenylene ether ether ketone) is recovered in the form of a mixed solid with the linear poly (phenylene ether ether ketone). Since a solvent having such properties generally has a relatively high property and preferred solvents vary depending on the types of the organic polar solvent and by-product salt, the solvent cannot be restricted; however, examples thereof include water; alcohols represented by methanol, ethanol, propanol, isopropanol, butanol and hexanol; ketones represented by acetone and

[Formula 14]

(a)
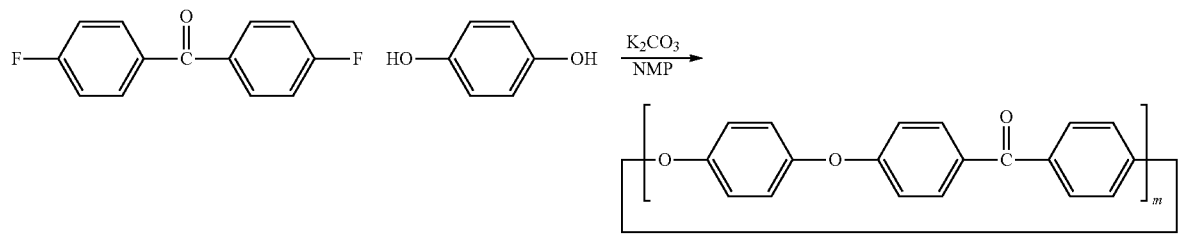

(b)
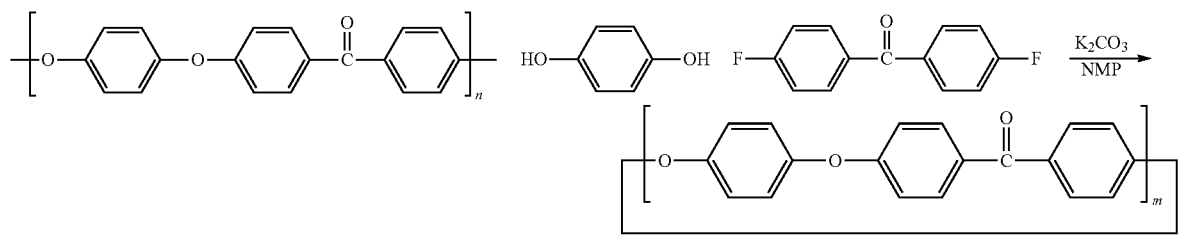

(c)
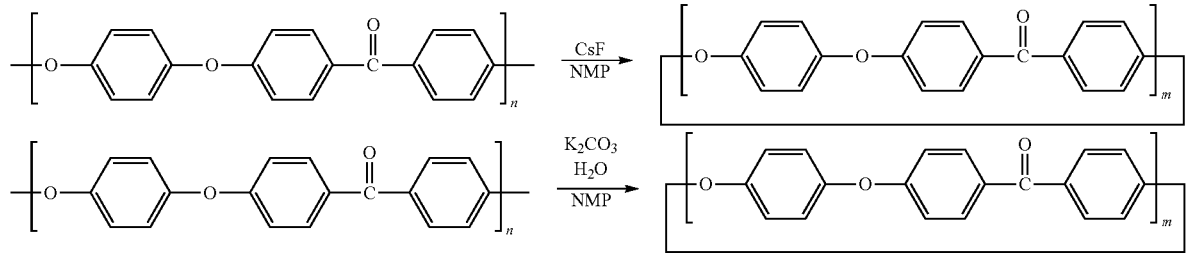

(9) Method of Recovering Cyclic Poly (Phenylene Ether Ether Ketone) Composition

The cyclic poly (phenylene ether ether ketone) composition according to the present invention can be separated and recovered from a reaction mixture obtained by the respective production methods described in the above section (8). The reaction mixture obtained by the above-described respective production methods contains at least a cyclic poly (phenylene methyl ethyl ketone; and acetic acid esters represented by ethyl acetate and butyl acetate, and from the standpoints of the availability and economic efficiency, water, methanol and acetone are preferred and water is particularly preferred.

By performing a treatment with such solvent, the amounts of the organic polar solvent and by-product salt contained in the mixed solid of cyclic poly (phenylene ether ether ketone) and linear poly (phenylene ether ether ketone) can be reduced. This treatment precipitates both the cyclic poly (phenylene ether ether ketone) and linear poly (phenylene ether ether ketone) as solid components; therefore, the resulting mixture of the cyclic poly (phenylene ether ether ketone) and linear poly (phenylene ether ether ketone) can be recovered by a known solid-liquid separation method, so that the amounts of the organic polar solvent and by product salt contained in the mixed solid of the cyclic poly (phenylene ether ether ketone) and linear poly (phenylene ether ether ketone) tends to be further reduced.

In addition, as the above-described treatment method using a solvent, a method in which a solvent and reaction mixture are mixed may be employed, and the resulting mixture may also be appropriately stirred or heated as required. The temperature at which such treatment with a solvent is performed is not particularly restricted; however, it is preferably 20 to 220° C., more preferably 50 to 200° C. It is preferred that the temperature be in such a range because, for example, the by-product salt can be easily removed and the treatment can be performed under a relatively low pressure. Here, in cases where water is used as the solvent, it is preferred that the water be distilled water or deionized water; however, as required, an aqueous solution which contains, for example, an organic acid compound such as formic acid, acetic acid, propionic acid, butyric acid, chloroacetic acid, dichloroacetic acid, acrylic acid, crotonic acid, benzoic acid, salicylic acid, oxalic acid, malonic acid, succinic acid, phthalic acid or fumaric acid and an alkali metal salt or alkaline earth metal salt thereof, or an inorganic acid compound such as sulfuric acid, phosphoric acid, hydrochloric acid, carbonic acid or silicic acid and ammonium ions may also be employed. In cases where the thus obtained mixed solid of cyclic poly (phenylene ether ether ketone) and linear poly (phenylene ether ether ketone) contains the solvent used in the treatment, drying or the like may also be performed to eliminate the solvent.

In the above-described recovery method, the cyclic poly (phenylene ether ether ketone) is recovered in the form of a mixture with the linear poly (phenylene ether ether ketone) to obtain a cyclic poly (phenylene ether ether ketone) composition. Examples of the method of separating and recovering the cyclic poly (phenylene ether ether ketone) from this mixture for the purpose of further increasing the content thereof in the resulting composition include a method which utilizes the difference in the solubility between the cyclic poly (phenylene ether ether ketone) and linear poly (phenylene ether ether ketone), and more specific examples include a method in which a solvent having a high solubility for the cyclic poly (phenylene ether ether ketone) and a poor solubility for the linear poly (phenylene ether ether ketone) is brought into contact with the above-described mixture of the cyclic poly (phenylene ether ether ketone) and linear poly (phenylene ether ether ketone) under heating as required to obtain the cyclic poly (phenylene ether ether ketone) as a solvent-soluble component. In general, linear poly (phenylene ether ether ketone)s are known to have characteristics of being highly crystalline and having an extremely low solubility to a solvent and there is a large difference between the solvent solubility of a cyclic poly (phenylene ether ether ketone) and that of a linear poly (phenylene ether ether ketone). Therefore, a cyclic poly (phenylene ether ether ketone) can be obtained more efficiently by a separation method which utilizes the above-described difference in the solubility.

The solvent used here is not particularly restricted as long as it is capable of dissolving a cyclic poly (phenylene ether ether ketone); however, it is preferably one which dissolves a cyclic poly (phenylene ether ether ketone) but hardly dissolves a linear poly (phenylene ether ether ketone) under the conditions for performing the dissolution, more preferably one which does not dissolve a linear poly (phenylene ether ether ketone). When bringing the mixture of cyclic poly (phenylene ether ether ketone) and linear poly (phenylene ether ether ketone) into contact with the above-described solvent, the pressure of the reaction system is preferably normal pressure or a slightly increased pressure, and a reaction system having such a pressure is advantageous in that the members of the reactor constituting the reaction system are inexpensive. From these standpoints, for the pressure of the reaction system, it is desired that an increased pressure condition requiring an expensive pressure-resistant container be avoided. The solvent used here is preferably one which does not substantially cause undesirable side reactions such as decomposition and cross-linking of the poly (phenylene ether ether ketone) components. In cases where the above-described operation of bringing the mixture into contact with a solvent is performed under, for example, reflux conditions at normal pressure, examples of preferred solvent include hydrocarbon-based solvents such as pentane, hexane, heptane, octane, cyclohexane, cyclopentane, benzene, toluene and xylene; halogen-based solvents such as chloroform, bromoform, methylene chloride, 1,2-dichloroethane, 1,1,1-trichloroethane, chlorobenzene and 2,6-dichlorotoluene; ether-based solvents such as diethyl ether, tetrahydrofuran and diisopropyl ether; and polar solvents such as N,N-dimethylformamide, N,N-dimethylacetamide, dimethyl sulfoxide, trimethyl phosphate and N,N-dimethylimidazolidinone. Thereamong, benzene, toluene, xylene chloroform, bromoform, methylene chloride, 1,2-dichloroethane, 1,1,1-trichloroethane, chlorobenzene, 2,6-dichlorotoluene, diethyl ether, tetrahydrofuran, diisopropyl ether, N,N-dimethylformamide, N,N-dimethylacetamide, dimethyl sulfoxide, trimethyl phosphate and N,N-dimethylimidazolidinone are preferred, and toluene, xylene, chloroform, methylene chloride and tetrahydrofuran are more preferred.

The atmosphere in which the mixture composed of cyclic poly (phenylene ether ether ketone) and linear poly (phenylene ether ether ketone) is brought into contact with the solvent is not particularly restricted; however, it is preferably a non-oxidizing atmosphere. It is more preferred that this process be performed in an inert atmosphere such as nitrogen, helium or argon and, from the standpoints of the economic efficiency and ease of handling, this process is particularly preferably performed in a nitrogen atmosphere.

The temperature at which the above-described mixture composed of cyclic poly (phenylene ether ether ketone) and linear poly (phenylene ether ether ketone) is brought into contact with the solvent is not particularly restricted; however, in general, dissolution of a cyclic poly (phenylene ether ether ketone) in a solvent tends to be more facilitated at a higher temperature. As described in the above, the mixture composed of cyclic poly (phenylene ether ether ketone) and linear poly (phenylene ether ether ketone) is suitably brought into contact with the solvent at normal pressure; thus, the upper limit of the temperature therefor is preferably the reflux temperature of the used solvent under atmospheric pressure. In cases where the above-described preferred solvent is used, specific range of the temperature is, for example, 20 to 150° C.

The duration of the contact between the mixture composed of cyclic poly (phenylene ether ether ketone) and linear poly (phenylene ether ether ketone) and the solvent cannot be uniquely restricted since it varies depending on the type and temperature of the solvent used and the like; however, for example, the contact may be performed for 1 minute to 50 hours, and in such a range, the cyclic poly (phenylene ether ether ketone) tends to be sufficiently dissolved in the solvent.

The method of contacting the above-described mixture with the solvent is not particularly restricted and any known common technique may be employed, and examples thereof include a method in which, after mixing the mixture composed of cyclic poly (phenylene ether ether ketone) and linear poly (phenylene ether ether ketone) with the solvent and stirring the resultant as required, the resulting solution part is recovered; a method in which the cyclic poly (phenylene ether ether ketone) is dissolved in the solvent while showering the solvent over the above-described mixture on various filters at the same time; and a method based on the principles of Soxhlet extraction method. The amount of the solvent to be contacted with the mixture composed of cyclic poly (phenylene ether ether ketone) and linear poly (phenylene ether ether ketone) is not particularly restricted; however, it is, for example, in the range of 0.5 to 100 in terms of the liquor ratio to the weight of the mixture. When the liquor ratio is in such a range, it is easy to uniformly mix the above-described mixture with the solvent and it tends to be easy to sufficiently dissolve the cyclic poly (phenylene ether ether ketone) in the solvent. In general, a higher liquor ratio is more advantageous for dissolving a cyclic poly (phenylene ether ether ketone) in a solvent; however, an excessively large liquor ratio is not expected to have any further effect and rather, it may cause an economical drawback due to an increase in the amount of the solvent to be used. Here, in cases where the contact between the mixture and the solvent is repetitively performed, even at a small liquor ratio, sufficient effects can be attained in many cases, and also in cases where the Soxhlet extraction method is employed, since, in principle, similar effects can be attained, sufficient effects can often be attained even at a small liquor ratio.

When the mixture of cyclic poly (phenylene ether ether ketone) and linear poly (phenylene ether ether ketone) is brought into contact with the solvent and then the resulting solution, in which the cyclic poly (phenylene ether ether ketone) is dissolved, is obtained in the form of a solid-liquid slurry containing solid-form linear poly (phenylene ether ether ketone), it is preferred that the solution part be recovered by a known solid-liquid separation method. Examples of the solid-liquid separation method include separation by filtration, centrifugation and decantation. By removing the solvent from the thus separated solution, the cyclic poly (phenylene ether ether ketone) can be recovered. Meanwhile, as for the solid component, in cases where the cyclic poly (phenylene ether ether ketone) still remains therein, by repeating the steps of contacting it with the solvent and recovering the resulting solution, the cyclic poly (phenylene ether ether ketone) can be obtained in a higher yield.

The cyclic poly (phenylene ether ether ketone) can be obtained as a solid component by removing the solvent from the solution obtained in the above-described manner which contains the cyclic poly (phenylene ether ether ketone). Examples of the method of removing the solvent include a method in which the solution is heated and then treated at normal pressure and a method in which a membrane is used to remove the solvent; however, from the standpoint of obtaining the cyclic poly (phenylene ether ether ketone) in a higher yield and more efficiently, a method in which the solvent is removed by heating at a pressure not higher than normal pressure is preferred. Here, the solution obtained in the above-described manner, which contains the cyclic poly (phenylene ether ether ketone), may also contain a solid matter depending on the temperature; however, in this case, since the solid matter also belongs to the cyclic poly (phenylene ether ether ketone), it is preferred to recover the solid matter along with other solvent-soluble component(s) at the time of removing the solvent, and by doing so, the cyclic poly (phenylene ether ether ketone) can be obtained in a higher yield. It is preferred that at least not less than 50% by weight, preferably not less than 70% by weight, more preferably not less than 90% by weight, still more preferably not less than 95% by weight of the solvent be removed. The temperature at which the solvent is removed by heating cannot be uniquely restricted since it depends on the type of the solvent used; however, it may be selected to be in the range of usually 20 to 150° C., preferably 40 to 120° C. Further, the removal of the solvent is preferably performed at a pressure not higher than normal pressure, so that the solvent can be removed at a lower temperature.

As described in the section (1), the cyclic poly (phenylene ether ether ketone) composition obtained by the method of present invention is usually a highly pure composition which contains a cyclic poly (phenylene ether ether ketone) in an amount of not less than 60% by weight and has a high industrial utility value for having properties that are different from those of a linear poly (phenylene ether ether ketone).

(10) Method of Producing Poly (Phenylene Ether Ether Ketone)

The cyclic poly (phenylene ether ether ketone) composition can be used as a poly (phenylene ether ether ketone) prepolymer and converted into a poly (phenylene ether ether ketone) by thermal ring-opening polymerization. Here, the "poly (phenylene ether ether ketone)" refers to a linear compound represented by the above-described Formula (II), which has p-phenylene ketone and p-phenylene ether as repeating structural unit. Further, the reduced viscosity (n) of the poly (phenylene ether ether ketone) obtained by thermal ring-opening polymerization of the cyclic poly (phenylene ether ether ketone) composition according to the present invention is not particularly restricted; however, it is, for example, in the range of preferably 0.1 to 2.5 dL/g, more preferably 0.2 to 2.0 dL/g, still more preferably 0.3 to 1.8 dL/g.

When performing thermal ring-opening polymerization to convert the cyclic poly (phenylene ether ether ketone) composition into a poly (phenylene ether ether ketone), the heating temperature is preferably not lower than the melting temperature of the cyclic poly (phenylene ether ether ketone) composition and it is not particularly restricted as long as such temperature condition is attained. When the heating temperature is lower than the melting temperature of the cyclic poly (phenylene ether ether ketone) composition, it is required that the thermal ring-opening polymerization be performed for a prolonged period in order to obtain a poly (phenylene ether ether ketone), or the thermal ring-opening polymerization does not progress, so that a poly (phenylene ether ether ketone) may not be obtained. The melting temperature of the cyclic poly (phenylene ether ether ketone) composition cannot be uniquely stated here since it varies depending on the constitution and molecular weight of the cyclic poly (phenylene ether ether ketone) and the weight ratio of the cyclic poly (phenylene ether ether ketone) contained in the cyclic poly (phenylene ether ether ketone) composition as well as the condition at the time of heating; however, the melting temperature can be determined by, for example, analyzing the cyclic poly (phenylene ether ether ketone) composition using a differential scanning calorimeter. The lower limit of the heating temperature is, for example, not lower than 150° C., preferably not lower than 180° C., more preferably not lower than 200° C., still more preferably not lower than 220° C. The cyclic poly (phenylene ether ether ketone) composition is melted in this temperature range, so that a poly (phenylene ether ether ketone) tends to be obtained in a short time. Meanwhile, when the thermal ring-opening polymerization is performed at an excessively high temperature, undesirable side reactions represented by cross-linking reactions (e.g. those between cyclic poly (phenylene ether ether ketone)s, between the poly (phenylene ether ether ketone)s produced by the heating and between the poly (phenylene ether ether ketone) and cyclic poly (phenylene ether ether ketone) and decomposition reactions tend to occur easily and the properties of the resulting poly (phenylene ether ether ketone) may be impaired; therefore, it is desired to avoid performing the thermal ring-opening polymerization at a temperature where such undesirable side reactions occur prominently. The upper limit of the heating temperature is, for example, not higher than 500° C., preferably not higher than 400° C., more preferably not higher than 360° C., still more preferably not higher than 335° C., yet still more preferably not higher than 300° C. When the heating temperature is not higher than this range, those adverse effects on the properties of the resulting poly (phenylene ether ether ketone) caused by undesirable side reactions tend to be inhibited. In cases where a known cyclic poly (phenylene ether ether ketone) is used, since the melting point thereof is high, with the heating temperature being in the above-described preferred range, the thermal ring-opening polymerization is required to be performed for a prolonged period, or it does not progress, so that a poly (phenylene ether ether ketone) may not be obtained. On the other hand, in the case of the cyclic poly (phenylene ether ether ketone) composition according to the present invention, which is characterized by having a melting point of not higher than 270° C., the thermal ring-opening polymerization progresses efficiently in the above-described preferred temperature range, so that a poly (phenylene ether ether ketone) is obtained. In the method of producing a poly (phenylene ether ether ketone) according to the present invention, it is also possible to perform the thermal ring-opening polymerization at a temperature not lower than the melting point of the resulting poly (phenylene ether ether ketone).

The reaction time cannot be generally prescribed since it varies depending on the weight ratio and composition ratio of the cyclic poly (phenylene ether ether ketone) contained in the cyclic poly (phenylene ether ether ketone) composition to be used as well as the conditions such as the heating temperature and the method of thermal ring-opening polymerization; however, it is preferred that the reaction time be set such that the above-described undesirable side reactions such as cross-linking reactions do not take place. The reaction time is, for example, in the range of 0.01 to 100 hours, preferably 0.05 to 20 hours, more preferably 0.05 to 10 hours. By setting the reaction time in this preferably range, those adverse effects on the properties of the resulting poly (phenylene ether ether ketone) caused by undesirable side reactions such as cross-linking reactions tend to be inhibited.

In the method of producing a poly (phenylene ether ether ketone) by thermal ring-opening polymerization of the cyclic poly (phenylene ether ether ketone) composition according to the present invention, the thermal ring-opening polymerization can be performed in either the absence or presence of a catalyst. Here, the catalyst is not particularly restricted as long as it is a compound having an effect to accelerate the thermal ring-opening polymerization reaction of the cyclic poly (phenylene ether ether ketone) composition according to the present invention. As the catalyst, a known catalyst such as photo-polymerization initiator, radical polymerization initiator, cationic polymerization initiator, anionic polymerization initiator or transition-metal catalyst may be used, and preferred thereamong is an anionic polymerization initiator. Examples of the anionic polymerization initiator include inorganic alkali metal salts and organic alkali metal salts, and examples of the inorganic alkali metal salt include alkali metal halides such as sodium fluoride, potassium fluoride, cesium fluoride and lithium chloride. Further, examples of the organic alkali metal salt include alkali metal alkoxides such as sodium methoxide, potassium methoxide, sodium ethoxide, potassium ethoxide, sodium tert-butoxide and potassium tert-butoxide; alkali metal phenoxides such as sodium phenoxide, potassium phenoxide, sodium-4-phenoxyphenoxide and potassium-4-phenoxyphenoxide; and alkali metal acetates such as lithium acetate, sodium acetate and potassium acetate. It is speculated that these anionic polymerization initiators express a catalytic action by nucleophilically attacking the cyclic poly (phenylene ether ether ketone) composition. Therefore, a compound having a capability of nucleophilic attack comparable to that of these anionic polymerization initiators can also be used as the catalyst, and examples of such compound include polymers with anionically polymerizable terminals. These anionic polymerization initiators may be used individually, or two or more thereof may be used in combination. When thermal ring-opening polymerization of the cyclic poly (phenylene ether ether ketone) composition is performed in the presence of such preferred catalyst(s), a poly (phenylene ether ether ketone) tends to be obtained in a short time, and specifically, the heating time for the thermal ring-opening polymerization may be, for example, no longer than 2 hours, not longer than 1 hour, or not longer than 0.5 hour.

The amount of the catalyst to be used varies depending on the molecular weight of the desired poly (phenylene ether ether ketone) and the type of the catalyst; however, it is usually 0.001 to 20 mol %, preferably 0.005 to 15 mol %, more preferably 0.01 to 10 mol %, with respect to 1 mol of the repeating unit represented by the following formula, which is the major structural unit of cyclic poly (phenylene ether ether ketone):

[Formula 15]

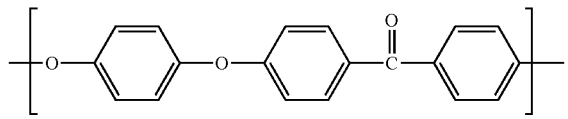

When the catalyst(s) is/are added in an amount in this preferred range, the thermal ring-opening polymerization of the cyclic poly (phenylene ether ether ketone) composition tends to progress in a short time.

With regard to the addition of the catalyst, it may be added as is; however, it is preferred that the catalyst be added to the cyclic poly (phenylene ether ether ketone) composition and then uniformly dispersed therein. Examples of method of uniformly dispersing the catalyst include a method in which the dispersed is attained mechanically and a method in which the catalyst is dispersed using a solvent. Specific examples of the method of mechanically dispersing the catalyst include those methods utilizing a grinder, stirrer, mixer, shaker or mortar. Further, specific examples of the method of dispersing the catalyst using a solvent include a method in which the cyclic poly (phenylene ether ether ketone) composition is dissolved or dispersed in an appropriate solvent and then the catalyst is added, followed by removal of the solvent. Further, in cases where a solid catalyst is added, it is preferred that the polymerization catalyst has an average particle size of not larger than 1 mm since such a size allows more uniform dispersion.

The thermal ring-opening polymerization of the cyclic poly (phenylene ether ether ketone) composition can be performed either in a solvent or in a condition which does not substantially include a solvent; however, it is preferably performed in a condition which does not substantially include a solvent since the temperature can be increased in a short time and the reaction rate is fast, so that a poly (phenylene ether ether ketone) tends to be easily obtained in a short time. Here, the "condition which does not substantially include a solvent" refers to a condition in which the solvent is contained in the cyclic poly (phenylene ether ether ketone) composition in an amount of not greater than 20% by weight, preferably not greater than 10% by weight, more preferably not greater than 5% by weight.

Further, it is needless to say that the heating may be performed using a conventional polymerization reactor. The heating method is not particularly restricted as long as an apparatus equipped with a heating mechanism is employed, and for example, the heating may also be performed in a mold used for producing molded articles or using an extruder or melt-kneading machine. Moreover, a known batch-wise method or continuous method can also be employed.

The atmosphere in which the thermal ring-opening polymerization of the cyclic poly (phenylene ether ether ketone) composition is performed is preferably a non-oxidizing atmosphere and it is also preferred to perform the thermal ring-opening polymerization under a reduced pressure condition. Further, in cases where the thermal ring-opening polymerization is performed under a reduced pressure condition, it is preferred that the atmosphere in the reaction system be made non-oxidizing first before reducing the pressure. By doing so, the occurrence of undesirable side reactions (e.g. cross-linking reactions between cyclic poly (phenylene ether ether ketone)s, between the poly (phenylene ether ether ketone)s produced by the thermal ring-opening polymerization and between the poly (phenylene ether ether ketone) and cyclic poly (phenylene ether ether ketone); and decomposition reactions) tends to be suppressed. Here, the "non-oxidizing atmosphere" refers to an atmosphere in which the gas phase contacting the cyclic poly (phenylene ether ether ketone) contains oxygen at a concentration of not higher than 5% by volume, preferably not higher than 2% by volume, more preferably contains substantially no oxygen, that is, an inert gas atmosphere such as nitrogen, helium or argon. Thereamong, from the standpoints of the economic efficiency and ease of handling, a nitrogen atmosphere is particularly preferred. Furthermore, the "reduced pressure condition" refers to a condition in which the pressure inside the system where the reaction is performed is lower than the atmospheric pressure, and the upper limit of the pressure is preferably not higher than 50 kPa, more preferably not higher than 20 kPa, still more preferably not higher than 10 kPa. The lower limit of the pressure is, for example, not lower than 0.1 kPa, more preferably not lower than 0.2 kPa. When the pressure is not below the preferred lower limit, vaporization of low-molecular-weight cyclic compound contained in the cyclic poly (phenylene ether ether ketone) composition hardly occurs, while when the pressure is not higher than the preferred upper limit, undesirable side reactions such as cross-linking reaction do not tend to occur easily.

The above-described heating of cyclic poly (phenylene ether ether ketone) can also be performed in the presence of a fibrous substance. Here, the "fibrous substance" refers to a fine filamentous substance and it is preferably an arbitrary substance having a narrowly elongated structure as in a natural fiber. By converting the cyclic poly (phenylene ether ether ketone) composition into a poly (phenylene ether ether ketone) in the presence of such fibrous substance, a composite material structure composed of the poly (phenylene ether ether ketone) and fibrous substance can be easily prepared. Since such a structure is reinforced by the fibrous substance, it tends to have, for example, superior mechanical and physical properties as compared to the case of using the poly (phenylene ether ether ketone) alone.

Here, among a variety of fibrous substances, it is preferred to use a reinforced fiber made of a long-staple fiber, and by doing so, the poly (phenylene ether ether ketone) can be highly reinforced. In general, in the production of a composite material structure composed of a resin and fibrous material, the wetting between the resin and fibrous material tends to be poor since the viscosity of the resin becomes high when it is melted; therefore, in many cases, a uniform composite material cannot be obtained and the mechanical and physical properties are not expressed as expected. The term "wetting" used herein means a condition where, in the physical states of a fluid substance such as molten resin and a solid substrate such as fibrous compound, a good contact is maintained in such a manner that substantially no air or other gas is trapped between the fluid substance and the solid substance. Here, the lower the viscosity of the fluid substance, the better the wetting thereof with the fibrous substance tends to become. The cyclic poly (phenylene ether ether ketone) composition according to the present invention has, when melted, a considerably lower viscosity as compared to common thermoplastic resins such as poly (phenylene ether ether ketone); therefore, the wetting thereof with a fibrous substance tends to be good. According to the method of producing a poly (phenylene ether ether ketone) of the present invention, the cyclic poly (phenylene ether ether ketone) composition is converted into a poly (phenylene ether ether ketone) after a good wetting condition is formed between the cyclic poly (phenylene ether ether ketone) composition and a fibrous substance; therefore, a composite material structure in which a good wetting condition is formed between the fibrous substance and poly (phenylene ether ether ketone) can be easily obtained.

As described in the above, as the fibrous substance, a reinforced fiber made of a long-staple fiber is preferred. The reinforced fiber used in the present invention is not particularly restricted, and examples of reinforced fibers that can be suitably used include those fibers having good heat resistance and tensile strength that are commonly used as a high-performance reinforced fiber. Examples of such reinforced fiber include glass fibers, carbon fibers, graphite fibers, aramid fibers, silicon carbide fibers, alumina fibers and boron fibers. Thereamong, the most preferred are, for example, those carbon fibers and graphite fibers that have good specific strength and specific modulus and are recognized to largely contribute to weight saving. A variety of carbon fibers and graphite fibers can be used depending on the intended used thereof; however, a high-strength, high-ductile carbon fiber having a tensile strength of 450 Kgf/mm$^2$ and a tensile ductility of not less than 1.6% is most suitably used. When a reinforced fiber in the form of a long-staple fiber is used, the length thereof is preferably not shorter than 5 cm. At such length, the strength of the reinforced fiber is easily and sufficiently expressed as a composite material. Further, a carbon fiber or graphite fiber may also be used by mixing it with other reinforced fiber. Moreover, the shape and arrangement of the reinforced fiber are not restricted, and for example, the reinforced fiber may be of unidirectional orientation or random orientation and in a sheet-form, mat-form, woven-form or brade-form. Furthermore, for an application which requires particularly high specific strength and specific modulus, a reinforced fiber having unidirectional arrangement is most appropriately used, and in the present invention, a reinforced fiber arranged in the form of a cloth (fabric), which has good ease of handling, is also suitably used.

Further, the above-described conversion of the cyclic poly (phenylene ether ether ketone) composition into a poly (phenylene ether ether ketone) can also be performed in the presence of a filler. Examples of the filler include non-fibrous glasses, non-fibrous carbons and inorganic fillers such as calcium carbonate, titanium oxide and alumina.

(11) Use of Cyclic Poly (Phenylene Ether Ether Ketone) Composition

When blended in a thermoplastic resin, the cyclic poly (phenylene ether ether ketone) composition according to the present invention has a strong tendency to largely reduce the melt viscosity of the thermoplastic resin and exhibit an effect to improve the fluidity of the thermoplastic resin. This effect is exhibited because a cyclic poly (phenylene ether ether ketone) is different from ordinary linear compounds and linear polymers in that it does not have a terminal structure, so that the level of the intermolecular entanglement is low.

Here, the thermoplastic resin may be any resin as long as it can be melt-molded, and examples thereof include polyamide resins; polyester resins; polyacetal resins; polycarbonate resins; poly phenylene ether resins; modified poly phenylene ether resins produced by blending or graft-polymerizing a poly phenylene ether resin and other resin; polyarylate resins; polysulfone resins; poly phenylene sulfide resins; polyethersulfone resins; polyketone resins; polyether ketone resins; polyether ether ketone resins; polyimide resins; polyamide imide resins; polyetherimide resins; thermoplastic polyurethane resins; high-density polyethylene resins; low-density polyethylene resins; linear low-density polyethylene resins; polypropylene resins; polymethylpentene resins; cyclic olefin-based resins; poly-1-butene resins; poly-1-pentene resins; polymethylpentene resins; ethylene/α-olefin copolymers; copolymers of (ethylene and/or propylene) and (unsaturated carboxylic acid and/or unsaturated carboxylic ester); polyolefins obtained by converting at least a part of the carboxyl group in a copolymer of (ethylene and/or propylene) and (unsaturated carboxylic acid and/or unsaturated carboxylic ester) into a metal salt; block copolymers of conjugated diene and vinyl aromatic hydrocarbon; hydrides thereof; polyvinyl chloride resins; polystyrene resins; acrylic resins such as polyacrylate resins and polymethacrylate resins; acrylonitrile-based copolymers whose major component is acrylonitrile; acrylonitrile-butadiene-styrene (ABS) resins; acrylonitrile-styrene (AS) resins; cellulose-based resins such as cellulose acetate resins; vinyl chloride/ethylene copolymers; vinyl chloride/vinyl acetate copolymers; ethylene/vinyl acetate copolymers; and saponification product of ethylene/vinyl acetate copolymers. These resins may be used individually, or two or more thereof may be used in combination as a polymer alloy.

The cyclic poly (phenylene ether ether ketone) composition according to the present invention can be mixed with the above-described thermoplastic resin(s) at any arbitrary ratio; however, for example, the thermoplastic resin(s) and the cyclic poly (phenylene ether ether ketone) composition are mixed at a ratio of, respectively, preferably 70 to 99.9% by weight and 0.1 to 30% by weight, more preferably 90 to 99.9% by weight and 0.1 to 10% by weight, still more preferably 95 to 99.5% by weight and 0.5 to 5% by weight.

As the method of producing such a thermoplastic resin composition comprising the cyclic poly (phenylene ether ether ketone) composition according to the present invention and thermoplastic resin, a method utilizing melt-kneading is preferred, and any known method can be employed for the melt-kneading. For example, a Banbury mixer, rubber roller, kneader or single-/twin-screw extruder can be used for melt-kneading the thermoplastic resin and the cyclic poly (phenylene ether ether ketone) composition at a temperature not lower than their melting temperatures to obtain a resin composition. Thereamong, a twin-screw extruder is exemplified as a preferred method. As the kneading method, any kneading method may be employed, and examples thereof include 1) a method in which the thermoplastic resin and the cyclic poly (phenylene ether ether ketone) are kneaded all together at once; and 2) a method in which a resin composition (master pellet) containing the cyclic poly (phenylene ether ether ketone) in the thermoplastic resin at a high concentration is prepared and then the thus obtained resin composition and the thermoplastic resin are added to a prescribed concentration and the resultant is melt-kneaded (master pellet method). The cyclic poly (phenylene ether ether ketone) composition according to the present invention is characterized by having a low melting point of not higher than 270° C. Therefore, since the melt-kneading for the production of thermoplastic resin composition can be set at such a temperature, the melt-kneading with a thermoplastic resin tends to be easily performed.

The thermoplastic resin composition obtained in this manner can be normally molded by an arbitrary known method such as injection molding, injection compression molding, compression molding, extrusion molding, blow molding, press molding or spinning and processed into a variety of molded articles to be used. Examples of the molded articles include injection-molded articles, extrusion-molded articles, blow-molded articles, films, sheets and fibers. The films can be utilized in a variety of forms including unstretched film, uniaxially-stretched film and biaxially-stretched film, and the fibers can also be utilized in a variety of forms including undrawn yarn, drawn yarn and super-drawn yarn.

EXAMPLES

The present invention will now be described more concretely by way of examples thereof. These examples are provided for illustrative purposes and form no restriction on the present invention.

Here, a variety of physical properties were measured by high-performance liquid chromatography, differential scanning calorimeter (DSC), infrared spectrophotometer (IR) and Ostwald viscosimeter, and quantitative analyses of cyclic poly (phenylene ether ether ketone)s were performed using high-performance liquid chromatography. The details of the analytical conditions are as follows.

(High-Performance Liquid Chromatography)
Apparatus: LC-10Avp Series manufactured by SHIMADZU
Column: Mightysil RP-18GP150-4.6
Detector: photodiode array detector (using UV=270 nm)
Column temperature: 40° C.
Sample: 0.1% by weight THF solution
Mobile phase: THF/0.1 w% aqueous trifluoroacetate solution
(Differential Scanning Calorimeter)
Apparatus: Robot DSC manufactured by Seiko Instruments Inc.
(Infrared Spectrophotometer)
Apparatus: Perkin Elmer System 2000 FT-IR
Sample preparation: KBr method (Viscosity Measurement)
Viscometer: Ostwald viscosimeter
Solvent: 98% by weight sulfuric acid
Sample concentration: 0.1 g/dL (sample weight/solvent volume)
Measuring temperature: 25° C.
Reduced viscosity calculation equation: $\eta=\{(t/t0)-1\}/C$
t: sample solution transit time (in seconds)
t0: solvent transit time (in seconds)
C: solution concentration Example 1

Method (a) of Producing Cyclic Poly (Phenylene Ether Ether Ketone) Composition

To a four-necked flask equipped with a stirrer, nitrogen inlet tube, Dean-Stark apparatus, condenser tube and thermometer, 2.40 g (11 mmol) of 4,4'-difluorobenzophenone, 1.10 g (10 mmol) of hydroquinone, 1.52 g (11 mmol) of anhydrous potassium carbonate, 100 mL of dimethyl sulfoxide and 10 mL of toluene were loaded. The amount of the dimethyl sulfoxide with respect to 1.0 mol of the benzene ring component contained in the resulting mixture was 3.13 L. The temperature of the mixture was raised to 140° C. under nitrogen flow and maintained there for 1 hour. Then, the temperature was further raised to 160° C. and maintained there for 4 hours to allow the mixture to react. After completion of the reaction, the resultant was cooled to room temperature to prepare a reaction mixture.

About 0.2 g of the thus obtained reaction mixture was weighed and diluted with about 4.5 g of THF. Then, THF-insoluble component was separated and removed by filtration to prepare a sample for high-performance liquid chromatography analysis and the reaction mixture was analyzed. As a result, it was confirmed that 5 types of cyclic poly (phenylene ether ether ketone)s having consecutive repeating numbers of 2 to 6 were generated, and the yield of the cyclic poly (phenylene ether ether ketone) mixture was found to be 15.3% with respect to the hydroquinone.

Thereafter, 50 g of the thus obtained reaction mixture was recovered in a fraction of 50 g, and 150 g of 1% by weight aqueous acetic acid solution was added thereto. After making the resultant into a slurry by stirring, the slurry was heated to 70° C. and stirred for another 30 minutes. The resulting slurry was filtered through a glass filter (average pore size: 10 to 16 µm) to recover a solid content. Then, the steps of dispersing the thus recovered solid content in 50 g of deionized water; maintaining the resulting dispersion at 70° C. for 30 minutes; and filtering the resultant to obtain a solid content were repeated three times. The thus obtained solid content was vacuum-dried overnight at 70° C. to obtain about 1.24 g of dry solid.

Further, 1.0 g of the thus obtained dry solid was subjected to Soxhlet extraction with 100 g of chloroform for 5 hours at a bath temperature of 80° C. The chloroform was removed from the resulting extract using an evaporator to obtain a solid content. After adding 2 g of chloroform to this solid content, the resultant was made into a dispersion using an ultrasonic washer and added dropwise to 30 g of methanol. The resulting precipitate was separated by filtration using a filter paper having an average pore size of 1 µm and then vacuum-dried at 70° C. for 3 hours to obtain a white solid. The weight of the thus obtained white solid was 0.14 g and the yield thereof was 14.0% with respect to the hydroquinone used in the reaction.

From the absorption spectrum obtained by infrared spectrophotometry, this white powder was confirmed to be a compound composed of phenylene ether ketone units. In addition, from mass spectrometric analysis (apparatus: HITACHI M-1200H) of the components separated by high-performance liquid chromatography and the molecular weight information obtained by MALDI-TOF-MS, the white powder was determined to be a cyclic poly (phenylene ether ether ketone) composition comprising a mixture of 5 types of cyclic poly (phenylene ether ether ketone)s having consecutive repeating numbers (m) of 2 to 6. Moreover, the weight ratio of the cyclic poly (phenylene ether ether ketone) mixture in the cyclic poly (phenylene ether ether ketone) composition was 81%. It is noted here that the cyclic poly (phenylene ether ether ketone) composition also contained a linear poly (phenylene ether ether ketone) oligomer as a component other than cyclic poly (phenylene ether ether ketone).

The melting point of the cyclic poly (phenylene ether ether ketone) composition was measured to be 163° C. In addition, the reduced viscosity of the cyclic poly (phenylene ether ether ketone) composition was measured to be less than 0.02 dL/g.

Further, the chloroform-insoluble solid component, which was obtained in the above-described process of recovering the cyclic poly (phenylene ether ether ketone) composition by Soxhlet extraction, was vacuum-dried overnight at 70° C. to obtain about 0.85 g of off-white solid content. This off-white solid content was subjected to an infrared spectrophotometric analysis and from the thus obtained absorption spectrum, the off-white solid content was confirmed to be a linear poly (phenylene ether ether ketone). In addition, as a result of measuring the reduced viscosity, it was found that this linear poly (phenylene ether ether ketone) has a reduced viscosity of 0.45 dL/g.

Example 2

Method (a) of Producing Cyclic Poly (Phenylene Ether Ether Ketone) Composition

To a four-necked flask equipped with a stirrer, nitrogen inlet tube, Dean-Stark apparatus, condenser tube and thermometer, 2.76 g (11 mmol) of 4,4'-dichlorobenzophenone, 1.10 g (10 mmol) of hydroquinone, 1.52 g (11 mmol) of anhydrous potassium carbonate, 100 mL of dimethyl sulfoxide and 20 mL of toluene were loaded. The amount of the dimethyl sulfoxide with respect to 1.0 mol of the benzene ring component contained in the resulting mixture was 3.13 L. The temperature of the mixture was raised to 140° C. under nitrogen flow and maintained there for 1 hour. Then, the temperature was further raised to 160° C. and maintained there for 3 hours to allow the mixture to react. After completion of the reaction, the resultant was cooled to room temperature to prepare a reaction mixture.

About 0.2 g of the thus obtained reaction mixture was weighed and diluted with about 4.5 g of THF. Then, THF-insoluble component was separated and removed by filtration to prepare a sample for high-performance liquid chromatography analysis and the reaction mixture was analyzed. As a result, it was confirmed that a mixture of 5 types of cyclic poly (phenylene ether ether ketone)s having consecutive repeating numbers of 2 to 6 was generated, and the yield thereof was found to be 7.0% with respect to the hydroquinone.

Further, when the cyclic poly (phenylene ether ether ketone)s were recovered from the above-described reaction mixture in accordance with the method described in Example 1, the yield thereof was 7.8% with respect to the hydroquinone. As a result of analyzing the thus obtained cyclic poly (phenylene ether ether ketones), it was found that the weight ratio of the cyclic poly (phenylene ether ether ketone) mixture in the cyclic poly (phenylene ether ether ketone) composition was 69% and that the melting point thereof was about 180° C. Also, the reduced viscosity of the cyclic poly (phenylene ether ether ketone) composition was found to be less than 0.02 dL/g.

Example 3

Method (a) of Producing Cyclic Poly (Phenylene Ether Ether Ketone) Composition

To a four-necked flask equipped with a stirrer, nitrogen inlet tube, Dean-Stark apparatus, condenser tube and thermometer, 2.18 g (10 mmol) of 4,4'-difluorobenzophenone, 1.10 g (10 mmol) of hydroquinone, 1.38 g (10 mmol) of anhydrous potassium carbonate, 100 mL of N-methyl-2-pyrrolidone and 20 mL of toluene were loaded. The amount of the N-methyl-2-pyrrolidone with respect to 1.0 mol of the benzene ring component contained in the resulting mixture was 3.33 L. The temperature of the mixture was raised to 140° C. under nitrogen flow and maintained there for 1 hour. Then, the temperature was raised to 160° C. and maintained there for 3 hours, and the temperature was further raised to 195° C. and maintained there for 2 hours to allow the mixture to react. After completion of the reaction, the resultant was cooled to room temperature to prepare a reaction mixture.

About 0.2 g of the thus obtained reaction mixture was weighed and diluted with about 4.5 g of THF. Then, THF-insoluble component was separated and removed by filtration to prepare a sample for high-performance liquid chromatography analysis and the reaction mixture was analyzed. As a result, it was confirmed that a mixture of 7 types of cyclic poly (phenylene ether ether ketone)s having consecutive repeating numbers of 2 to 8 was generated, and the yield thereof was found to be 20.0% with respect to the hydroquinone.

Further, when the cyclic poly (phenylene ether ether ketone)s were recovered from the above-described reaction mixture in accordance with the method described in Example 1, the yield thereof was 18.7% with respect to the hydroquinone. As a result of analyzing the thus obtained cyclic poly (phenylene ether ether ketone)s, it was found that the weight ratio of the cyclic poly (phenylene ether ether ketone) mixture in the cyclic poly (phenylene ether ether ketone) composition was 78% and that the melting point thereof was 158° C. Also, the reduced viscosity of the cyclic poly (phenylene ether ether ketone) composition was found to be less than 0.02 dL/g.

From the above results and those results described in Example 1, it is understood that, by using an organic polar solvent in an amount of not less than 1.20 L with respect to 1.0 mol of the benzene ring component in the mixture, a cyclic poly (phenylene ether ether ketone) composition can be efficiently produced regardless of the type of the organic polar solvent and the reaction temperature; and that the resulting cyclic poly (phenylene ether ether ketone) composition has a melting point of not higher than 270° C.

Example 4

Method (a) of Producing Cyclic Poly (Phenylene Ether Ether Ketone) Composition

To a four-necked flask equipped with a stirrer, nitrogen inlet tube, Dean-Stark apparatus, condenser tube and thermometer, 6.98 g (32 mmol) of 4,4'-difluorobenzophenone, 3.30 g (30 mmol) of hydroquinone, 4.42 g (32 mmol) of anhydrous potassium carbonate, 140 mL of dimethyl sulfoxide and 20 mL of toluene were loaded. The amount of the dimethyl sulfoxide with respect to 1.0 mol of the benzene ring component contained in the resulting mixture was 1.49 L. The temperature of the mixture was raised to 140° C. under nitrogen flow and maintained there for 1 hour. Then, the temperature was further raised to 160° C. and maintained there for 4 hours to allow the mixture to react. After completion of the reaction, the resultant was cooled to room temperature to prepare a reaction mixture.

About 0.2 g of the thus obtained reaction mixture was weighed and diluted with about 4.5 g of THF. Then, THF-insoluble component was separated and removed by filtration to prepare a sample for high-performance liquid chromatography analysis and the reaction mixture was analyzed. As a result, it was confirmed that a mixture of 5 types of cyclic poly (phenylene ether ether ketone)s having consecutive repeating numbers of 2 to 6 was generated, and the yield thereof was found to be 9.8% with respect to the hydroquinone.

Further, when the cyclic poly (phenylene ether ether ketone)s were recovered from the above-described reaction mixture in accordance with the method described in Example 1, the yield thereof was 9.6% with respect to the hydroquinone. As a result of analyzing the thus obtained cyclic poly (phenylene ether ether ketone) composition, it was found that the weight ratio of the cyclic poly (phenylene ether ether ketone) mixture in the cyclic poly (phenylene ether ether ketone) composition was 81% and that the melting point thereof was 163° C. Also, the reduced viscosity of this cyclic poly (phenylene ether ether ketone) composition was found to be less than 0.02 dL/g.

From these results, it is understood that a cyclic poly (phenylene ether ether ketone) composition having a melting point of not higher than 270° C. can be obtained by setting the amount of the organic polar solvent with respect to 1.0 mol of the benzene ring component contained in the mixture (M1) in the above-described preferred range.

Example 5

Method (a) of Producing Cyclic Poly (Phenylene Ether Ether Ketone) Composition

To a 1-L autoclave equipped with a stirrer, 10.91 g (50 mmol) of 4,4'-difluorobenzophenone, 5.51 g (50 mmol) of hydroquinone, 6.91 g (50 mmol) of anhydrous potassium carbonate and 500 mL of N-methyl-2-pyrrolidone were loaded. The amount of the N-methyl-2-pyrrolidone with respect to 1.0 mol of the benzene ring component contained in the resulting mixture was 3.33 L.

After sealing the reaction vessel under nitrogen gas at room temperature and normal pressure, while stirring the mixture at 400 rpm, the temperature was raised from room temperature to 140° C. and maintained there for 1 hour. The temperature was then raised to 180° C. and maintained there for 3 hours, and subsequently, the temperature was further raised to 230° C. and maintained there for 5 hours to allow the mixture to react. After completion of the reaction, the resultant was cooled to room temperature to prepare a reaction mixture.

About 0.2 g of the thus obtained reaction mixture was weighed and diluted with about 4.5 g of THF. Then, THF-insoluble component was separated and removed by filtration to prepare a sample for high-performance liquid chromatography analysis and the reaction mixture was analyzed. As a result, it was confirmed that a mixture of 7 types of cyclic poly (phenylene ether ether ketone) having consecutive repeating numbers of 2 to 8 was generated, and the yield thereof was found to be 11.5% with respect to the hydroquinone.

Further, when the cyclic poly (phenylene ether ether ketone) composition was recovered from the above-described reaction mixture in accordance with the method described in Example 1, the yield thereof was 11.3% with respect to the hydroquinone. As a result of analyzing the thus obtained cyclic poly (phenylene ether ether ketone) composition, it was found that the weight ratio of the cyclic poly (phenylene ether ether ketone) mixture in the cyclic poly (phenylene ether ether ketone) composition was 85% and that the melting point thereof was 159° C. Also, the reduced viscosity of this cyclic poly (phenylene ether ether ketone) composition was found to be less than 0.02 dL/g.

From the above results and those results described in Example 1, it is understood that, by using an organic polar solvent in an amount of not less than 1.20 L with respect to 1.0 mol of the benzene ring component in the mixture, a cyclic poly (phenylene ether ether ketone) composition can be efficiently produced regardless of the type of the organic polar solvent and the reaction temperature; and that the resulting cyclic poly (phenylene ether ether ketone) composition has a melting point of not higher than 270° C.

Example 6

Method (a) of Producing Cyclic Poly (Phenylene Ether Ether Ketone) Composition

To a 1-L autoclave equipped with a stirrer, 10.91 g (50 mmol) of 4,4'-difluorobenzophenone, 5.51 g (50 mmol) of hydroquinone, 6.91 g (50 mmol) of anhydrous potassium carbonate and 500 mL of N-methyl-2-pyrrolidone were loaded. The amount of the N-methyl-2-pyrrolidone with respect to 1.0 mol of the benzene ring component contained in the resulting mixture was 3.33 L.

After sealing the reaction vessel under nitrogen gas at room temperature and normal pressure, while stirring the mixture at 400 rpm, the temperature was raised from room temperature to 140° C. and maintained there for 1 hour. The temperature was then raised to 180° C. and maintained there for 3 hours, and subsequently, the temperature was further raised to 250° C. and maintained there for 5 hours to allow the mixture to react. After completion of the reaction, the resultant was cooled to room temperature to prepare a reaction mixture.

About 0.2 g of the thus obtained reaction mixture was weighed and diluted with about 4.5 g of THF. Then, THF-insoluble component was separated and removed by filtration to prepare a sample for high-performance liquid chromatography analysis and the reaction mixture was analyzed. As a result, it was confirmed that 7 types of cyclic poly (phenylene ether ether ketone)s having consecutive repeating numbers of 2 to 8 were generated, and the yield of the cyclic poly (phenylene ether ether ketone) mixture was found to be 15.0% with respect to the hydroquinone.

Further, when the cyclic poly (phenylene ether ether ketone) composition was recovered from the above-described reaction mixture in accordance with the method described in Example 1, the yield thereof was 15.0% with respect to the hydroquinone. As a result of analyzing the thus obtained cyclic poly (phenylene ether ether ketone) composition, it was found that the weight ratio of the cyclic poly (phenylene ether ether ketone) mixture in the cyclic poly (phenylene ether ether ketone) composition was 88% and that the melting point thereof was 160° C. Also, the reduced viscosity of this cyclic poly (phenylene ether ether ketone) composition was found to be less than 0.02 dL/g.

From the above results, it is understood that, by using an organic polar solvent in an amount of not less than 1.20 L with respect to 1.0 mol of the benzene ring component in the mixture, a cyclic poly (phenylene ether ether ketone) composition can be efficiently produced regardless of the type of the organic polar solvent and the reaction temperature; and that the resulting cyclic poly (phenylene ether ether ketone) composition has a melting point of not higher than 270° C.

Example 7

Method (a) of Producing Cyclic Poly (Phenylene Ether Ether Ketone) Composition

To a 1-L autoclave equipped with a stirrer, 10.91 g (50 mmol) of 4,4'-difluorobenzophenone, 5.51 g (50 mmol) of hydroquinone, 6.91 g (50 mmol) of anhydrous potassium carbonate and 500 mL of N-methyl-2-pyrrolidone were loaded. The amount of the N-methyl-2-pyrrolidone with respect to 1.0 mol of the benzene ring component contained in the resulting mixture was 3.33 L.

After sealing the reaction vessel under nitrogen gas at room temperature and normal pressure, while stirring the mixture at 400 rpm, the temperature was raised from room temperature to 140° C. and maintained there for 1 hour. The temperature was then raised to 180° C. and maintained there for 3 hours, and subsequently, the temperature was further raised to 270° C. and maintained there for 5 hours to allow the mixture to react. After completion of the reaction, the resultant was cooled to room temperature to prepare a reaction mixture.

About 0.2 g of the thus obtained reaction mixture was weighed and diluted with about 4.5 g of THF. Then, THF-insoluble component was separated and removed by filtration to prepare a sample for high-performance liquid chromatography analysis and the reaction mixture was analyzed. As a result, it was confirmed that 7 types of cyclic poly (phenylene ether ether ketone)s having consecutive repeating numbers of 2 to 8 were generated, and the yield of the cyclic poly (phenylene ether ether ketone) mixture was found to be 14.9% with respect to the hydroquinone.

Further, when the cyclic poly (phenylene ether ether ketone) composition was recovered from the above-described reaction mixture in accordance with the method described in Example 1, the yield thereof was 14.5% with respect to the hydroquinone. As a result of analyzing the thus obtained cyclic poly (phenylene ether ether ketone) composition, it was found that the weight ratio of the cyclic poly (phenylene ether ether ketone) mixture in the cyclic poly (phenylene ether ether ketone) composition was 82% and that the melting point thereof was 162° C. Also, the reduced viscosity of this cyclic poly (phenylene ether ether ketone) composition was found to be less than 0.02 dL/g.

From the above results, it is understood that, by using an organic polar solvent in an amount of not less than 1.20 L with respect to 1.0 mol of the benzene ring component in the mixture, a cyclic poly (phenylene ether ether ketone) composition can be efficiently produced regardless of the type of the organic polar solvent and the reaction temperature; and that the resulting cyclic poly (phenylene ether ether ketone) composition has a melting point of not higher than 270° C.

Comparative Example 1

Here, poly (phenylene ether ether ketone) synthesis in accordance with the general method described in an example of JP 2007-506833A is described.

To a four-necked flask equipped with a stirrer, nitrogen inlet tube, Dean-Stark apparatus, condenser tube and thermometer, 22.5 g (103 mmol) of 4,4'-difluorobenzophenone, 11.0 g (100 mmol) of hydroquinone and 49 g of diphenyl sulfone were loaded. The amount of the diphenyl sulfone with respect to 1.0 mol of the benzene ring component contained in the resulting mixture was about 0.16 L. When the temperature was raised to 140° C. under nitrogen flow, a substantially colorless solution was formed. At this temperature, 10.6 g (100 mmol) of anhydrous sodium carbonate and 0.28 g (2 mmol) of anhydrous potasium carbonate were added. The temperature of the resultant was raised to 200° C. and maintained there for 1 hour, and was then raised to 250° C. and maintained there for 1 hour, before being further raised to 315° C. and maintained there for 3 hours.

As a result of analyzing the thus obtained reaction mixture by high-performance liquid chromatography, the yield of the cyclic poly (phenylene ether ether ketone) mixture with respect to the hydroquinone was a trace mount of less than 1%.

The reaction mixture was cooled and pulverized, and the resultant was then washed with water and acetone to remove by-product salts and diphenyl sulfone. The resulting polymer was dried in a hot air dryer at 120° C. to obtain powder.

Then, about 1.0 g of the thus obtained powder was subjected to Soxhlet extraction with 100 g of chloroform for 5 hours at a bath temperature of 80° C. The chloroform was removed from the resulting extract using an evaporator to obtain a small amount of chloroform-soluble component. The yield of the thus recovered chloroform-soluble component was 1.2% with respect to the hydroquinone used in the reaction. As a result of analyzing the recovered chloroform-soluble component by high-performance liquid chromatography, it was found that this chloroform-soluble component contained a cyclic poly (phenylene ether ether ketone) and linear poly (phenylene ether ether ketone) oligomer. This linear poly (phenylene ether ether ketone) oligomer is similar to a cyclic poly (phenylene ether ether ketone) in terms of its properties such as solvent solubility and is a compound which is difficult to be separated from cyclic poly (phenylene ether ether ketone). Further, the cyclic poly (phenylene ether ether ketone) mixture contained in the recovered chloroform-soluble component was composed of cyclic poly (phenylene ether ether ketone)s having the repeating numbers (m) of 4 and 5; and that the weight ratio of cyclic poly (phenylene ether ether ketone) having a repeating number (m) of 4 was not less than 80%. Moreover, the melting point of the recovered chloroform-soluble component was found to be about 320° C. This is speculated to be attributable to the high content of the tetrameric cyclic poly (phenylene ether ether ketone) (m=4) in the chloroform-soluble component obtained by this method.

Further, chloroform-insoluble solid component obtained in the above-described Soxhlet extraction was vacuum-dried overnight at 70° C. to obtain about 0.98 g of off-white solid content. This off-white solid content was subjected to an infrared spectrophotometric analysis and from the thus obtained absorption spectrum, the off-white solid content was confirmed to be a linear poly (phenylene ether ether ketone). In addition, as a result of measuring the reduced viscosity, it was found that this linear poly (phenylene ether ether ketone) has a reduced viscosity of 0.75 dL/g.

Comparative Example 2

To a four-necked flask equipped with a stirrer, nitrogen inlet tube, Dean-Stark apparatus, condenser tube and thermometer, 22.5 g (103 mmol) of 4,4'-difluorobenzophenone, 11.0 g (100 mmol) of hydroquinone, 13.8 g (100 mmol) of anhydrous potassium carbonate and 50 mL of dimethyl sulfoxide were loaded. The amount of the dimethyl sulfoxide with respect to 1.0 mol of the benzene ring component contained in the resulting mixture was 0.16 L. Under nitrogen flow, the temperature of the mixture was raised to 140° C. and maintained there for 1 hour, and was then raised to 160° C. and maintained there for 3 hours, before being further raised to 175° C. and maintained there for 5 hours to allow the mixture to react. However, since a large amount of polymer was precipitated in the early stage of the reaction, it was difficult to attain sufficient stirring.

As a result of analyzing the thus obtained reaction mixture by high-performance liquid chromatography, the yield of the cyclic poly (phenylene ether ether ketone) mixture with respect to the hydroquinone was a trace mount of less than 1%.

Further, when the chloroform-soluble component was recovered from the above-described reaction mixture in accordance with the method described in Example 1, the yield thereof was about 1.0% with respect to the hydroquinone. In addition, as a result of analyzing the thus obtained chloroform-soluble component, it was found that the weight ratio of the cyclic poly (phenylene ether ether ketone) mixture in the chloroform-soluble component was 46%. This is speculated to be attributable to that the reaction was incomplete due to the precipitation of polymer occurred during the reaction.

Comparative Example 3

To a 100-mL autoclave equipped with a stirrer, 22.5 g (103 mmol) of 4,4'-difluorobenzophenone, 11.0 g (100 mmol) of hydroquinone, 13.8 g (100 mmol) of anhydrous potassium carbonate and 50 mL of N-methyl-2-pyrrolidone were loaded. The amount of the N-methyl-2-pyrrolidone with respect to 1.0 mol of the benzene ring component contained in the resulting mixture was 0.16 L.

After sealing the reaction vessel under nitrogen gas at room temperature and normal pressure, while stirring the mixture at 400 rpm, the temperature of the mixture was raised to 140° C. and maintained there for 1 hour, and was then raised to 180° C. and maintained there for 3 hours, before being further raised to 230° C. and maintained there for 5 hours to allow the mixture to react. However, because of defective stirring occurred in the early stage of the reaction, it was difficult to attain sufficient stirring. This is speculated to be attributable to the precipitation of polymer occurred in the early stage of the reaction.

As a result of analyzing the thus obtained reaction mixture by high-performance liquid chromatography, the yield of the cyclic poly (phenylene ether ether ketone) mixture with respect to the hydroquinone was a trace mount of less than 1%.

Further, when the chloroform-soluble component was recovered from the above-described reaction mixture in accordance with the method described in Example 1, the yield thereof was about 0.8% with respect to the hydroquinone. In addition, as a result of analyzing the thus obtained chloroform-soluble component, it was found that the weight ratio of the cyclic poly (phenylene ether ether ketone) mixture in the chloroform-soluble component was 53%. As in the case of Comparative Example 2, these results are also speculated to be attributable to that the reaction was incomplete due to the precipitation of polymer occurred during the reaction.

Example 8

Method (b) of Producing Cyclic Poly (Phenylene Ether Ether Ketone) Composition

In this Example 8, the method (b) of producing a cyclic poly (phenylene ether ether ketone) using the linear poly (phenylene ether ether ketone) (reduced viscosity: 0.75 dL/g) obtained by the method of Comparative Example 1 is described.

To a 100-mL autoclave equipped with a stirrer, 0.22 g (1 mmol) of 4,4'-difluorobenzophenone, 0.11 g (1 mmol) of hydroquinone, 0.14 g (1 mmol) of anhydrous potassium carbonate, 1.15 g (4 mmol) of the linear poly (phenylene ether ether ketone) obtained by the method described in Comparative Example 1 and 50 mL of N-methyl-2-pyrrolidone were loaded. The amount of the N-methyl-2-pyrrolidone with respect to 1.0 mol of the benzene ring component contained in the resulting mixture was 3.33 L.

After sealing the reaction vessel under nitrogen gas at room temperature and normal pressure, while stirring the mixture at 400 rpm, the temperature was raised from room temperature to 140° C. and maintained there for 1 hour. The temperature was then raised to 180° C. and maintained there for 3 hours, and subsequently, the temperature was further raised to 230° C. and maintained there for 5 hours to allow the mixture to react.

About 0.2 g of the thus obtained reaction mixture was weighed and diluted with about 4.5 g of THF. Then, THF-insoluble component was separated and removed by filtration to prepare a sample for high-performance liquid chromatography analysis and the reaction mixture was analyzed. As a result, it was confirmed that 7 types of cyclic poly (phenylene ether ether ketone)s having consecutive repeating numbers of 2 to 8 were generated, and the yield of the cyclic poly (phenylene ether ether ketone) mixture was found to be 8.0% (here, the yield of the cyclic poly (phenylene ether ether ketone) mixture was calculated by comparing the amount of the benzene ring component contained in the thus produced cyclic poly (phenylene ether ether ketone) mixture and that of the benzene ring component contained in the poly (phenylene ether ether ketone), hydroquinone and 4,4'-difluorobenzophenone that were used in the reaction).

Further, when the cyclic poly (phenylene ether ether ketone) composition was recovered from the above-described reaction mixture in accordance with the method described in Example 1, the cyclic poly (phenylene ether ether ketone) composition was obtained in a yield of 7.8%. As a result of analyzing the thus obtained cyclic poly (phenylene ether ether ketone) composition, it was found that the weight ratio of the cyclic poly (phenylene ether ether ketone) mixture in the cyclic poly (phenylene ether ether ketone) composition was 78% and that the melting point thereof was 163° C. Also, the reduced viscosity of this cyclic poly (phenylene ether ether ketone) composition was found to be less than 0.02 dL/g.

From the above results, it is understood that, in the production method (b) as well, a cyclic poly (phenylene ether ether ketone) composition can be efficiently produced by using the organic polar solvent in an amount of not less than 1.20 L with respect to 1.0 mol of the benzene ring component in the mixture; and that the resulting cyclic poly (phenylene ether ether ketone) composition has a melting point of not higher than 270° C.

Example 9

Method (b) of Producing Cyclic Poly (Phenylene Ether Ether Ketone) Composition

In this Example 9, the method (b) of producing a cyclic poly (phenylene ether ether ketone) using the linear poly (phenylene ether ether ketone) (reduced viscosity: 0.75 dL/g) obtained by the method of Comparative Example 1 is described.

To a 100-mL autoclave equipped with a stirrer, 0.11 g (0.5 mmol) of 4,4'-difluorobenzophenone, 0.06 g (0.5 mmol) of hydroquinone, 0.07 g (0.5 mmol) of anhydrous potassium carbonate, 1.30 g (4.5 mmol) of the linear poly (phenylene ether ether ketone) obtained by the method described in Comparative Example 1 and 50 mL of N-methyl-2-pyrrolidone were loaded. The amount of the N-methyl-2-pyrrolidone with respect to 1.0 mol of the benzene ring component contained in the resulting mixture was 3.33 L.

After sealing the reaction vessel under nitrogen gas at room temperature and normal pressure, while stirring the mixture at 400 rpm, the temperature was raised from room temperature to 140° C. and maintained there for 1 hour. The temperature was then raised to 180° C. and maintained there for 3 hours, and subsequently, the temperature was further raised to 230° C. and maintained there for 5 hours to allow the mixture to react.

About 0.2 g of the thus obtained reaction mixture was weighed and diluted with about 4.5 g of THF. Then, THF-insoluble component was separated and removed by filtration to prepare a sample for high-performance liquid chromatography analysis and the reaction mixture was analyzed. As a result, it was confirmed that 7 types of cyclic poly (phenylene ether ether ketone)s having consecutive repeating numbers of 2 to 8 were generated, and the yield of the cyclic poly (phenylene ether ether ketone) mixture was found to be 7.8% (here, the yield of the cyclic poly (phenylene ether ether ketone) mixture was calculated by comparing the amount of the benzene ring component contained in the thus produced cyclic poly (phenylene ether ether ketone) mixture and that of the benzene ring component contained in the poly (phenylene ether ether ketone), hydroquinone and 4,4'-difluorobenzophenone that were used in the reaction).

Further, when the cyclic poly (phenylene ether ether ketone) composition was recovered from the above-described reaction mixture in accordance with the method described in Example 1, the cyclic poly (phenylene ether ether ketone) composition was obtained in a yield of 7.5%. As a result of analyzing the thus obtained cyclic poly (phenylene ether ether ketone) composition, it was found that the weight ratio of the cyclic poly (phenylene ether ether ketone) mixture in the cyclic poly (phenylene ether ether ketone) composition was 79% and that the melting point thereof was 166° C. Also, the reduced viscosity of this cyclic poly (phenylene ether ether ketone) composition was found to be less than 0.02 dL/g.

From the above results, it is understood that, in the production method (b) as well, by using the organic polar solvent in an amount of not less than 1.20 L with respect to 1.0 mol of the benzene ring component in the mixture, a cyclic poly (phenylene ether ether ketone) composition can be efficiently produced regardless of the ratio between the poly (phenylene ether ether ketone) and difluorobenzophenone that are used in the reaction; and that the resulting cyclic poly (phenylene ether ether ketone) composition has a melting point of not higher than 270° C.

Example 10

Method (b) of Producing Cyclic Poly (Phenylene Ether Ether Ketone) Composition

In this Example 10, the method (b) of producing a cyclic poly (phenylene ether ether ketone) using the linear poly (phenylene ether ether ketone) (reduced viscosity: 0.75 dL/g) obtained by the method of Comparative Example 1 is described.

To a 100-mL autoclave equipped with a stirrer, 0.22 g (1 mmol) of 4,4'-difluorobenzophenone, 0.11 g (1 mmol) of hydroquinone, 0.14 g (1 mmol) of anhydrous potassium carbonate, 1.15 g (4 mmol) of the linear poly (phenylene ether ether ketone) obtained by the method described in Comparative Example 1 and 50 mL of N-methyl-2-pyrrolidone were loaded. The amount of the N-methyl-2-pyrrolidone with respect to 1.0 mol of the benzene ring component contained in the resulting mixture was 3.33 L.

After sealing the reaction vessel under nitrogen gas at room temperature and normal pressure, while stirring the mixture at 400 rpm, the temperature was raised from room temperature to 140° C. and maintained there for 1 hour. The temperature was then raised to 180° C. and maintained there for 3 hours, and subsequently, the temperature was further raised to 270° C. and maintained there for 5 hours to allow the mixture to react.

About 0.2 g of the thus obtained reaction mixture was weighed and diluted with about 4.5 g of THF. Then, THF-insoluble component was separated and removed by filtration to prepare a sample for high-performance liquid chromatography analysis and the reaction mixture was analyzed. As a result, it was confirmed that 7 types of cyclic poly (phenylene ether ether ketone)s having consecutive repeating numbers of 2 to 8 were generated, and the yield of the cyclic poly (phenylene ether ether ketone) mixture was found to be 12.2% (here, the yield of the cyclic poly (phenylene ether ether ketone) mixture was calculated by comparing the amount of the benzene ring component contained in the thus produced cyclic poly (phenylene ether ether ketone) mixture and that of the benzene ring component contained in the poly (phenylene ether ether ketone), hydroquinone and 4,4'-difluorobenzophenone that were used in the reaction).

Further, when the cyclic poly (phenylene ether ether ketone) composition was recovered from the above-described reaction mixture in accordance with the method described in Example 1, the cyclic poly (phenylene ether ether ketone) composition was obtained in a yield of 12.0%. As a result of analyzing the thus obtained cyclic poly (phenylene ether ether ketone) composition, it was found that the weight ratio of the cyclic poly (phenylene ether ether ketone) mixture in the cyclic poly (phenylene ether ether ketone) composition was 80% and that the melting point thereof was 163° C. Also, the reduced viscosity of this cyclic poly (phenylene ether ether ketone) composition was found to be less than 0.02 dL/g.

From the above results, it is understood that, in the production method (b) as well, a cyclic poly (phenylene ether ether ketone) composition can be efficiently produced by using the organic polar solvent in an amount of not less than 1.20 L with respect to 1.0 mol of the benzene ring component in the mixture; and that the resulting cyclic poly (phenylene ether ether ketone) composition has a melting point of not higher than 270° C.

Example 11

Method (b) of Producing Cyclic Poly (Phenylene Ether Ether Ketone) Composition

In this Example 11, the method (b) of producing a cyclic poly (phenylene ether ether ketone) using the linear poly (phenylene ether ether ketone) (reduced viscosity: 0.75 dL/g) obtained by the method of Comparative Example 1 is described.

To a 100-mL autoclave equipped with a stirrer, 0.11 g (0.5 mmol) of 4,4'-difluorobenzophenone, 0.06 g (0.5 mmol) of hydroquinone, 0.07 g (0.5 mmol) of anhydrous potassium carbonate, 1.30 g (4.5 mmol) of the linear poly (phenylene ether ether ketone) obtained by the method described in Comparative Example 1 and 50 mL of N-methyl-2-pyrrolidone were loaded. The amount of the N-methyl-2-pyrrolidone with respect to 1.0 mol of the benzene ring component contained in the resulting mixture was 3.33 L.

After sealing the reaction vessel under nitrogen gas at room temperature and normal pressure, while stirring the mixture at 400 rpm, the temperature was raised from room temperature to 140° C. and maintained there for 1 hour. The temperature was then raised to 180° C. and maintained there for 3 hours, and subsequently, the temperature was further raised to 270° C. and maintained there for 5 hours to allow the mixture to react.

About 0.2 g of the thus obtained reaction mixture was weighed and diluted with about 4.5 g of THF. Then, THF-insoluble component was separated and removed by filtration to prepare a sample for high-performance liquid chromatography analysis and the reaction mixture was analyzed. As a result, it was confirmed that 7 types of cyclic poly (phenylene ether ether ketone)s having consecutive repeating numbers of 2 to 8 were generated, and the yield of the cyclic poly (phenylene ether ether ketone) mixture was found to be 12.0% (here, the yield of the cyclic poly (phenylene ether ether ketone) mixture was calculated by comparing the amount of the benzene ring component contained in the thus produced cyclic poly (phenylene ether ether ketone) mixture and that of the benzene ring component contained in the poly (phenylene ether ether ketone), hydroquinone and 4,4'-difluorobenzophenone that were used in the reaction).

Further, when the cyclic poly (phenylene ether ether ketone) composition was recovered from the above-described reaction mixture in accordance with the method described in Example 1, the cyclic poly (phenylene ether ether ketone) composition was obtained in a yield of 11.5%. As a result of analyzing the thus obtained cyclic poly (phenylene ether ether ketone) composition, it was found that the weight ratio of the cyclic poly (phenylene ether ether ketone) mixture in the cyclic poly (phenylene ether ether ketone) composition was 79% and that the melting point thereof was 168° C. Also, the reduced viscosity of this cyclic poly (phenylene ether ether ketone) composition was found to be less than 0.02 dL/g.

From the above results, it is understood that, in the production method (b) as well, by using the organic polar solvent in an amount of not less than 1.20 L with respect to 1.0 mol of the benzene ring component in the mixture, a cyclic poly (phenylene ether ether ketone) composition can be efficiently produced regardless of the ratio between the poly (phenylene ether ether ketone) and difluorobenzophenone that are used in the reaction; and that the resulting cyclic poly (phenylene ether ether ketone) composition has a melting point of not higher than 270° C.

Example 12

Method (b) of producing cyclic poly (phenylene ether ether ketone) composition

In this Example 12, the method (b) of producing a cyclic poly (phenylene ether ether ketone) using the linear poly (phenylene ether ether ketone) produced as a by-product in the above-described method of producing a cyclic poly (phenylene ether ether ketone) composition is described.

To a 100-mL autoclave equipped with a stirrer, 0.22 g (1 mmol) of 4,4'-difluorobenzophenone, 0.11 g (1 mmol) of hydroquinone, 0.14 g (1 mmol) of anhydrous potassium carbonate, 1.15 g (4 mmol) of the linear poly (phenylene ether ether ketone) (reduced viscosity: 0.45 dL/g) obtained by the method described in Example 1 and 50 mL of N-methyl-2-pyrrolidone were loaded. The amount of the N-methyl-2-pyrrolidone with respect to 1.0 mol of the benzene ring component contained in the resulting mixture was 3.33 L.

After sealing the reaction vessel under nitrogen gas at room temperature and normal pressure, while stirring the mixture at 400 rpm, the temperature was raised from room temperature to 140° C. and maintained there for 1 hour. The temperature was then raised to 180° C. and maintained there for 3 hours, and subsequently, the temperature was further raised to 230° C. and maintained there for 5 hours to allow the mixture to react.

About 0.2 g of the thus obtained reaction mixture was weighed and diluted with about 4.5 g of THF. Then, THF-insoluble component was separated and removed by filtration to prepare a sample for high-performance liquid chromatography analysis and the reaction mixture was analyzed. As a result, it was confirmed that 7 types of cyclic poly (phenylene ether ether ketone)s having consecutive repeating numbers of 2 to 8 were generated, and the yield of the cyclic poly (phenylene ether ether ketone) mixture was found to be 8.3%.

Further, when the cyclic poly (phenylene ether ether ketone) composition was recovered from the above-described reaction mixture in accordance with the method described in Example 1, the cyclic poly (phenylene ether ether ketone) composition was obtained in a yield of 8.0%. As a result of analyzing the thus obtained cyclic poly (phenylene ether ether ketone) composition, it was found that the weight ratio of the cyclic poly (phenylene ether ether ketone) mixture in the cyclic poly (phenylene ether ether ketone) composition was 77% and that the melting point thereof was 165° C. Also, the reduced viscosity of this cyclic poly (phenylene ether ether ketone) composition was found to be less than 0.02 dL/g.

From the above results, it is understood that, in the production method (b), a cyclic poly (phenylene ether ether ketone) composition can be efficiently produced regardless of the reduced viscosity, that is, polymerization degree, of the linear poly (phenylene ether ether ketone) used; and that the resulting cyclic poly (phenylene ether ether ketone) composition has a melting point of not higher than 270° C.

Example 13

Method (b) of Producing Cyclic Poly (Phenylene Ether Ether Ketone) Composition

In this Example 13, the method (b) of producing a cyclic poly (phenylene ether ether ketone) using the linear poly (phenylene ether ether ketone) produced as a by-product in the above-described method of producing a cyclic poly (phenylene ether ether ketone) composition is described.

To a 100-mL autoclave equipped with a stirrer, 0.22 g (1 mmol) of 4,4'-difluorobenzophenone, 0.11 g (1 mmol) of hydroquinone, 0.14 g (1 mmol) of anhydrous potassium carbonate, 1.15 g (4 mmol) of the linear poly (phenylene ether ether ketone) (reduced viscosity: 0.45 dL/g) obtained by the method described in Example 1 and 50 mL of N-methyl-2-pyrrolidone were loaded. The amount of the N-methyl-2-pyrrolidone with respect to 1.0 mol of the benzene ring component contained in the resulting mixture was 3.33 L.

After sealing the reaction vessel under nitrogen gas at room temperature and normal pressure, while stirring the mixture at 400 rpm, the temperature was raised from room temperature to 140° C. and maintained there for 1 hour. The temperature was then raised to 180° C. and maintained there for 3 hours, and subsequently, the temperature was further raised to 250° C. and maintained there for 5 hours to allow the mixture to react.

About 0.2 g of the thus obtained reaction mixture was weighed and diluted with about 4.5 g of THF. Then, THF-insoluble component was separated and removed by filtration to prepare a sample for high-performance liquid chromatography analysis and the reaction mixture was analyzed. As a result, it was confirmed that 7 types of cyclic poly (phenylene ether ether ketone)s having consecutive repeating numbers of 2 to 8 were generated, and the yield of the cyclic poly (phenylene ether ether ketone) mixture was found to be 8.5%.

Further, when the cyclic poly (phenylene ether ether ketone) composition was recovered from the above-described reaction mixture in accordance with the method described in Example 1, the cyclic poly (phenylene ether ether ketone) composition was obtained in a yield of 8.4%. As a result of analyzing the thus obtained cyclic poly (phenylene ether ether ketone) composition, it was found that the weight ratio of the cyclic poly (phenylene ether ether ketone) mixture in the cyclic poly (phenylene ether ether ketone) composition was 81% and that the melting point thereof was 168° C. Also, the reduced viscosity of this cyclic poly (phenylene ether ether ketone) composition was found to be less than 0.02 dL/g.

From the above results, it is understood that, in the production method (b), a cyclic poly (phenylene ether ether ketone) composition can be efficiently produced regardless of the reduced viscosity, that is, polymerization degree, of the linear poly (phenylene ether ether ketone) used; and that the resulting cyclic poly (phenylene ether ether ketone) composition has a melting point of not higher than 270° C.

Example 14

Method (b) of Producing Cyclic Poly (Phenylene Ether Ether Ketone) Composition

In this Example 14, the method (b) of producing a cyclic poly (phenylene ether ether ketone) using the linear poly (phenylene ether ether ketone) produced as a by-product in the above-described method of producing a cyclic poly (phenylene ether ether ketone) composition is described.

To a 100-mL autoclave equipped with a stirrer, 0.22 g (1 mmol) of 4,4'-difluorobenzophenone, 0.11 g (1 mmol) of hydroquinone, 0.14 g (1 mmol) of anhydrous potassium carbonate, 1.15 g (4 mmol) of the linear poly (phenylene ether ether ketone) (reduced viscosity: 0.45 dL/g) obtained by the method described in Example 1 and 50 mL of N-methyl-2-pyrrolidone were loaded. The amount of the N-methyl-2-pyrrolidone with respect to 1.0 mol of the benzene ring component contained in the resulting mixture was 3.33 L.

After sealing the reaction vessel under nitrogen gas at room temperature and normal pressure, while stirring the mixture at 400 rpm, the temperature was raised from room temperature to 140° C. and maintained there for 1 hour. The temperature was then raised to 180° C. and maintained there for 3 hours, and subsequently, the temperature was further raised to 270° C. and maintained there for 5 hours to allow the mixture to react.

About 0.2 g of the thus obtained reaction mixture was weighed and diluted with about 4.5 g of THF. Then, THF-insoluble component was separated and removed by filtration to prepare a sample for high-performance liquid chromatography analysis and the reaction mixture was analyzed. As a result, it was confirmed that 7 types of cyclic poly (phenylene ether ether ketone)s having consecutive repeating numbers of 2 to 8 were generated, and the yield of the cyclic poly (phenylene ether ether ketone) mixture was found to be 9.7%.

Further, when the cyclic poly (phenylene ether ether ketone) composition was recovered from the above-described reaction mixture in accordance with the method described in Example 1, the cyclic poly (phenylene ether ether ketone) composition was obtained in a yield of 9.5%. As a result of analyzing the thus obtained cyclic poly (phenylene ether ether ketone) composition, it was found that the weight ratio of the cyclic poly (phenylene ether ether ketone) mixture in the cyclic poly (phenylene ether ether ketone) composition was 78% and that the melting point thereof was 168° C. Also, the reduced viscosity of this cyclic poly (phenylene ether ether ketone) composition was found to be less than 0.02 dL/g.

From the above results, it is understood that, in the production method (b), a cyclic poly (phenylene ether ether ketone) composition can be efficiently produced regardless of the reduced viscosity, that is, polymerization degree, of the linear poly (phenylene ether ether ketone) used; and that the resulting cyclic poly (phenylene ether ether ketone) composition has a melting point of not higher than 270° C.

Example 15

In this Example 15, the method (b) of producing a cyclic poly (phenylene ether ether ketone) using the linear poly (phenylene ether ether ketone) produced as a by-product in the above-described method of producing a cyclic poly (phenylene ether ether ketone) composition is described.

To a 100-mL autoclave equipped with a stirrer, 0.11 g (0.5 mmol) of 4,4'-difluorobenzophenone, 0.06 g (0.5 mmol) of hydroquinone, 0.07 g (0.5 mmol) of anhydrous potassium carbonate, 1.30 g (4.5 mmol) of the linear poly (phenylene ether ether ketone) (reduced viscosity: 0.45 dL/g) obtained by the method described in Example 1 and 50 mL of N-methyl-2-pyrrolidone were loaded. The amount of the N-methyl-2-pyrrolidone with respect to 1.0 mol of the benzene ring component contained in the resulting mixture was 3.33 L.

After sealing the reaction vessel under nitrogen gas at room temperature and normal pressure, while stirring the mixture at 400 rpm, the temperature was raised from room temperature to 140° C. and maintained there for 1 hour. The temperature was then raised to 180° C. and maintained there for 3 hours, and subsequently, the temperature was further raised to 270° C. and maintained there for 5 hours to allow the mixture to react.

About 0.2 g of the thus obtained reaction mixture was weighed and diluted with about 4.5 g of THF. Then, THF-insoluble component was separated and removed by filtration to prepare a sample for high-performance liquid chromatography analysis and the reaction mixture was analyzed. As a result, it was confirmed that 7 types of cyclic poly (phenylene ether ether ketone)s having consecutive repeating numbers of 2 to 8 were generated, and the yield of the cyclic poly (phenylene ether ether ketone) mixture was found to be 10.6%.

Further, when the cyclic poly (phenylene ether ether ketone) composition was recovered from the above-described reaction mixture in accordance with the method described in Example 1, the cyclic poly (phenylene ether ether ketone) composition was obtained in a yield of 10.0%. As a result of analyzing the thus obtained cyclic poly (phenylene ether ether ketone) composition, it was found that the weight ratio of the cyclic poly (phenylene ether ether ketone) mixture in the cyclic poly (phenylene ether ether ketone) composition was 80% and that the melting point thereof was 163° C. Also, the reduced viscosity of this cyclic poly (phenylene ether ether ketone) composition was found to be less than 0.02 dL/g.

From the above results, it is understood that, in the production method (b), a cyclic poly (phenylene ether ether ketone) composition can be efficiently produced regardless of the reduced viscosity, that is, polymerization degree, of the linear poly (phenylene ether ether ketone) used; and that the resulting cyclic poly (phenylene ether ether ketone) composition has a melting point of not higher than 270° C.

Example 16

Method (c) of Producing Cyclic Poly (Phenylene Ether Ether Ketone) Composition

In this Example 16, the method (c) of producing a cyclic poly (phenylene ether ether ketone) using the linear poly (phenylene ether ether ketone) (reduced viscosity: 0.75 dL/g) obtained by the method of Comparative Example 1 is described.

To a 1-L autoclave equipped with a stirrer, 14.4 g (50 mmol) of the linear poly (phenylene ether ether ketone) obtained by the method described in Comparative Example 1, 1.52 g (10 mmol) of cesium fluoride and 500 mL of N-methyl-2-pyrrolidone were loaded. The amount of the N-methyl-2-pyrrolidone with respect to 1.0 mol of the benzene ring component contained in the resulting mixture was 3.33 L.

After sealing the reaction vessel under nitrogen gas at room temperature and normal pressure, while stirring the mixture at 400 rpm, the temperature was raised from room temperature to 140° C. and maintained there for 1 hour. The temperature was then raised to 180° C. and maintained there for 3 hours, and subsequently, the temperature was further raised to 230° C. and maintained there for 5 hours to allow the mixture to react.

About 0.2 g of the thus obtained reaction mixture was weighed and diluted with about 4.5 g of THF. Then, THF-insoluble component was separated and removed by filtration to prepare a sample for high-performance liquid chromatography analysis and the reaction mixture was analyzed. As a result, it was confirmed that 7 types of cyclic poly (phenylene ether ether ketone)s having consecutive repeating numbers of 2 to 8 were generated, and the yield of the cyclic poly (phenylene ether ether ketone) mixture was found to be 13.7% (here, the yield of the cyclic poly (phenylene ether ether ketone) mixture was calculated by comparing the amount of the thus produced cyclic poly (phenylene ether ether ketone)s and that of the poly (phenylene ether ether ketone) used in the reaction).

Further, when the cyclic poly (phenylene ether ether ketone) composition was recovered from the above-described reaction mixture in accordance with the method described in Example 1, the cyclic poly (phenylene ether ether ketone) composition was obtained in a yield of 13.7%. It was also found that the weight ratio of the cyclic poly (phenylene ether ether ketone) mixture in the thus obtained cyclic poly (phenylene ether ether ketone) composition was 79% and that the melting point thereof was 165° C. Moreover, the reduced viscosity of this cyclic poly (phenylene ether ether ketone) composition was found to be less than 0.02 dL/g.

From the above results, it is understood that, in the production method (c) as well, a cyclic poly (phenylene ether ether ketone) composition can be efficiently produced and the resulting cyclic poly (phenylene ether ether ketone) composition has a melting point of not higher than 270° C.

Example 17

Method (c) of Producing Cyclic Poly (Phenylene Ether Ether Ketone) Composition

In this Example 17, the method (c) of producing a cyclic poly (phenylene ether ether ketone) using the linear poly (phenylene ether ether ketone) produced as a by-product in the above-described method of producing a cyclic poly (phenylene ether ether ketone) composition is described.

To a 100-mL autoclave equipped with a stirrer, 1.44 g (5 mmol) of the linear poly (phenylene ether ether ketone) (reduced viscosity: 0.45 dL/g) obtained by the method described in Example 1, 0.15 g (1 mmol) of cesium fluoride and 50 mL of N-methyl-2-pyrrolidone were loaded. The amount of the N-methyl-2-pyrrolidone with respect to 1.0 mol of the benzene ring component contained in the resulting mixture was 3.33 L.

After sealing the reaction vessel under nitrogen gas at room temperature and normal pressure, while stirring the mixture at 400 rpm, the temperature was raised from room temperature to 140° C. and maintained there for 1 hour. The temperature was then raised to 180° C. and maintained there for 3 hours, and subsequently, the temperature was further raised to 230° C. and maintained there for 5 hours to allow the mixture to react.

About 0.2 g of the thus obtained reaction mixture was weighed and diluted with about 4.5 g of THF. Then, THF-insoluble component was separated and removed by filtration to prepare a sample for high-performance liquid chromatography analysis and the reaction mixture was analyzed. As a result, it was confirmed that 7 types of cyclic poly (phenylene ether ether ketones) having consecutive repeating numbers of 2 to 8 were generated, and the yield of the cyclic poly (phenylene ether ether ketone) mixture was found to be 14.0%.

Further, when the cyclic poly (phenylene ether ether ketone) composition was recovered from the above-described reaction mixture in accordance with the method described in Example 1, the cyclic poly (phenylene ether ether ketone) composition was obtained in a yield of 14.0%. It was also found that the weight ratio of the cyclic poly (phenylene ether ether ketone) mixture in the thus obtained cyclic poly (phenylene ether ether ketone) composition was 80% and that the melting point thereof was 165° C. Moreover, the reduced viscosity of this cyclic poly (phenylene ether ether ketone) composition was found to be less than 0.02 dL/g.

From the above results, it is understood that, in the production method (c) as well, a cyclic poly (phenylene ether ether ketone) composition can be efficiently produced regardless of the reduced viscosity, that is, polymerization degree, of the linear poly (phenylene ether ether ketone) used; and that the resulting cyclic poly (phenylene ether ether ketone) composition has a melting point of not higher than 270° C.

Example 18

Method (c) of Producing Cyclic Poly (Phenylene Ether Ether Ketone) Composition

In this Example 18, the method (c) of producing a cyclic poly (phenylene ether ether ketone) using the linear poly (phenylene ether ether ketone) (reduced viscosity: 0.75 dL/g) obtained by the method of Comparative Example 1 is described.

To a 1-L autoclave equipped with a stirrer, 14.4 g (50 mmol) of the poly (phenylene ether ether ketone) obtained by the method described in Comparative Example 1, 1.38 g (10 mmol) of anhydrous potassium carbonate, 1.0 g (56 mmol) of deionized water and 500 mL of N-methyl-2-pyrrolidone were loaded. The amount of the N-methyl-2-pyrrolidone with respect to 1.0 mol of the benzene ring component contained in the resulting mixture was 3.33 L.

After sealing the reaction vessel under nitrogen gas at room temperature and normal pressure, while stirring the mixture at 400 rpm, the temperature was raised from room temperature to 140° C. and maintained there for 1 hour. The temperature was then raised to 180° C. and maintained there for 3 hours, and subsequently, the temperature was further raised to 230° C. and maintained there for 5 hours to allow the mixture to react.

About 0.2 g of the thus obtained reaction mixture was weighed and diluted with about 4.5 g of THF. Then, THF-insoluble component was separated and removed by filtration to prepare a sample for high-performance liquid chromatography analysis and the reaction mixture was analyzed. As a result, it was confirmed that 7 types of cyclic poly (phenylene ether ether ketone)s having consecutive repeating numbers of 2 to 8 were generated, and the yield of the cyclic poly (phenylene ether ether ketone) mixture was found to be 13.4%.

Further, when the cyclic poly (phenylene ether ether ketone) composition was recovered from the above-described reaction mixture in accordance with the method described in Example 1, the cyclic poly (phenylene ether ether ketone) composition was obtained in a yield of 13.0%. It was also found that the weight ratio of the cyclic poly (phenylene ether ether ketone) mixture in the thus obtained cyclic poly (phenylene ether ether ketone) composition was 84% and that the melting point thereof was 160° C. Moreover, the reduced viscosity of this cyclic poly (phenylene ether ether ketone) composition was found to be less than 0.02 dL/g.

From the above results, it is understood that, in the production method (c) as well, a cyclic poly (phenylene ether ether ketone) composition can be efficiently produced and the resulting cyclic poly (phenylene ether ether ketone) composition has a melting point of not higher than 270° C.

Example 19

Method (c) of Producing Cyclic Poly (Phenylene Ether Ether Ketone) Composition

In this Example 19, the method (c) of producing a cyclic poly (phenylene ether ether ketone) using the linear poly (phenylene ether ether ketone) produced as a by-product in the above-described method of producing a cyclic poly (phenylene ether ether ketone) composition is described.

To a 100-mL autoclave equipped with a stirrer, 1.44 g (5 mmol) of the linear poly (phenylene ether ether ketone) (reduced viscosity: 0.45 dL/g) obtained by the method described in Example 1, 0.14 g (1 mmol) of anhydrous potassium carbonate, 0.1 g (6 mmol) of deionized water and 50 mL of N-methyl-2-pyrrolidone were loaded. The amount of the N-methyl-2-pyrrolidone with respect to 1.0 mol of the benzene ring component contained in the resulting mixture was 3.33 L.

After sealing the reaction vessel under nitrogen gas at room temperature and normal pressure, while stirring the mixture at 400 rpm, the temperature was raised from room temperature to 140° C. and maintained there for 1 hour. The temperature was then raised to 180° C. and maintained there for 3 hours, and subsequently, the temperature was further raised to 230° C. and maintained there for 5 hours to allow the mixture to react.

About 0.2 g of the thus obtained reaction mixture was weighed and diluted with about 4.5 g of THF. Then, THF-insoluble component was separated and removed by filtration to prepare a sample for high-performance liquid chromatography analysis and the reaction mixture was analyzed. As a result, it was confirmed that 7 types of cyclic poly (phenylene ether ether ketone)s having consecutive repeating numbers of 2 to 8 were generated, and the yield of the cyclic poly (phenylene ether ether ketone) mixture was found to be 13.5%.

Further, when the cyclic poly (phenylene ether ether ketone) composition was recovered from the above-described reaction mixture in accordance with the method described in Example 1, the cyclic poly (phenylene ether ether ketone) composition was obtained in a yield of 13.4%. It was also found that the weight ratio of the cyclic poly (phenylene ether ether ketone) mixture in the thus obtained cyclic poly (phenylene ether ether ketone) composition was 81% and that the melting point thereof was 162° C. Moreover, the reduced viscosity of this cyclic poly (phenylene ether ether ketone) composition was found to be less than 0.02 dL/g.

From the above results, it is understood that, in the production method (c) as well, a cyclic poly (phenylene ether ether ketone) composition can be efficiently produced regardless of the reduced viscosity, that is, polymerization degree, of the linear poly (phenylene ether ether ketone) used; and that the resulting cyclic poly (phenylene ether ether ketone) composition has a melting point of not higher than 270° C.

Example 20

Method of Producing Poly (Phenylene Ether Ether Ketone)

To the cyclic poly (phenylene ether ether ketone) composition obtained in Example 1, cesium fluoride was mixed in an amount of 5 mol % with respect to the repeating unit —(O-Ph-O-Ph-CO-Ph)-, which is the major structural unit of cyclic poly (phenylene ether ether ketone), to prepare 100 mg of powder. The thus obtained powder was loaded to a glass ampoule and the atmosphere therein was replaced with nitrogen. The ampoule was placed in an electric furnace having a controlled temperature of 350° C. and heated for 60 minutes. Then, the ampoule was taken out and cooled to room temperature to obtain black solid.

When the thus obtained black solid was analyzed using a differential scanning calorimeter, the block solid was found to have thermal properties such as a melting point of 332° C. and a crystallization temperature of 240° C. In addition, the reduced viscosity ($\eta$) of the black solid was measured to be 0.5 dL/g.

Example 21

Method of Producing Poly (Phenylene Ether Ether Ketone)

To the cyclic poly (phenylene ether ether ketone) composition obtained in Example 1, cesium fluoride was mixed in an amount of 5 mol % with respect to the repeating unit —(O-Ph-O-Ph-CO-Ph)-, which is the major structural unit of cyclic poly (phenylene ether ether ketone), to prepare 100 mg of powder. The thus obtained powder was loaded to a glass ampoule and the atmosphere therein was replaced with nitrogen. The ampoule was placed in an electric furnace having a controlled temperature of 300° C. and heated for 60 minutes. Then, the ampoule was taken out and cooled to room temperature to obtain black solid.

When the thus obtained black solid was analyzed using a differential scanning calorimeter, the block solid was found to have thermal properties such as a melting point of 347° C. and a crystallization temperature of 246° C. In addition, the reduced viscosity ($\eta$) of the black solid was measured to be 0.5 dL/g.

The invention claimed is:

1. A cyclic poly (phenylene ether ether ketone) composition, which comprises not less than 60% by weight of a cyclic poly (phenylene ether ether ketone) represented by the following Formula (I):

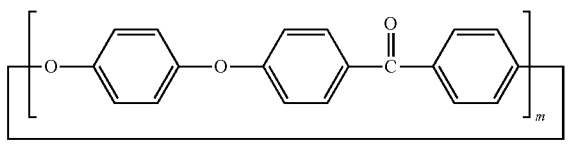

wherein, m represents an integer of 2 to 40;
said cyclic poly (phenylene ether ether ketone) being a mixture of cyclic poly (phenylene ether ether ketone)s having different repeating numbers (m) and said composition having a melting point of not higher than 270° C.

2. The cyclic poly (phenylene ether ether ketone) composition according to claim 1, wherein said cyclic poly (phenylene ether ether ketone) is a mixture composed of cyclic poly (phenylene ether ether ketone)s having at least 3 different integers (m).

3. The cyclic poly (phenylene ether ether ketone) composition according to claim 1, wherein said cyclic poly (phenylene ether ether ketone) is a mixture composed of cyclic poly (phenylene ether ether ketone)s having at least 3 consecutive different integers (m).

4. The cyclic poly (phenylene ether ether ketone) composition according to claim 1, wherein the composition has a reduced viscosity of not higher than 0.1 dL/g, said reduced viscosity being measured in sulfuric acid at 25° C.

5. The cyclic poly (phenylene ether ether ketone) composition according to claim 1, wherein said cyclic poly (phenylene ether ether ketone) is a mixture composed of cyclic poly (phenylene ether ether ketone)s having at least 5 consecutive different integers from 2 to 6 (m).

6. A method of producing a poly (phenylene ether ether ketone), wherein the cyclic poly (phenylene ether ether ketone) composition according to claim 1 is subjected to thermal ring-opening polymerization.

7. The method of producing a poly (phenylene ether ether ketone) according to claim 6, wherein said thermal ring-opening polymerization is performed at a temperature not higher than the melting point of the resulting poly (phenylene ether ether ketone).

8. The method of producing a poly (phenylene ether ether ketone) according to claim 6, wherein said thermal ring-opening polymerization is performed in the presence or absence of a catalyst.

9. The method of producing a poly (phenylene ether ether ketone) according to claim 8, wherein said catalyst is an anionic polymerization initiator.

10. A method of producing the cyclic poly (phenylene ether ether ketone) composition according to claim 1, wherein when a mixture (M1) comprising at least a dihalogenated aromatic ketone compound, dihydroxy aromatic compound, base (A) and organic polar solvent is allowed to react by heating to produce said cyclic poly (phenylene ether ether ketone) composition, said organic polar solvent is used in an amount of not less than 1.20 L with respect to 1.0 mol of benzene ring component in said mixture (M1).

11. The method of producing said cyclic poly (phenylene ether ether ketone) composition according to claim 10, wherein said dihydroxy aromatic compound is hydroquinone.

12. A method of producing the cyclic poly (phenylene ether ether ketone) composition according to claim 1, wherein when a mixture (M2) comprising at least a linear poly (phenylene ether ether ketone) represented by the following Formula (II):

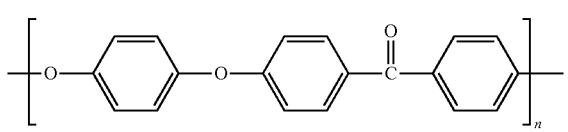
(II)

a dihalogenated aromatic ketone compound, a dihydroxy aromatic compound, a base (A) and an organic polar solvent is allowed to react by heating to produce said cyclic poly (phenylene ether ether ketone) composition, said organic polar solvent is used in an amount of not less than 1.20 L with respect to 1.0 mol of benzene ring component in said mixture (M2).

13. A method of producing the cyclic poly (phenylene ether ether ketone) composition according to claim 1, wherein a mixture (M3) comprising at least a linear poly (phenylene ether ether ketone) represented by the following Formula (II):

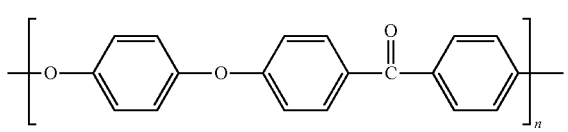
(II)

a basic compound (B) and an organic polar solvent is allowed to react by heating.

14. The method of producing said cyclic poly (phenylene ether ether ketone) composition according to claim 13, wherein said mixture (M3) further contains water.

15. The method of producing said cyclic poly (phenylene ether ether ketone) composition according to claim 13, wherein said basic compound (B) contained in said mixture (M3) is an alkali metal halide.

16. The method of producing said cyclic poly (phenylene ether ether ketone) composition according to claim 13, wherein said basic compound (B) contained in said mixture (M3) is an alkali metal carbonate and/or alkali metal bicarbonate.

17. A cyclic poly (phenylene ether ether ketone) composition produced according to a method of producing the cyclic poly (phenylene ether ether ketone) composition, which is characterized in that, when a mixture (M1) comprising at least a dihalogenated aromatic ketone compound, dihydroxy aromatic compound, base (A) and organic polar solvent is loaded at once and then heated to react to produce said cyclic poly (phenylene ether ether ketone) composition, said organic polar solvent is used in an amount of not less than 1.20 L and not more than 10 L with respect to 1.0 mol of benzene ring component in said mixture (M1), the cyclic poly (phenylene ether ether ketone) composition comprises not less than 60% by weight of a cyclic poly (phenylene ether ether ketone) represented by the following Formula (I):

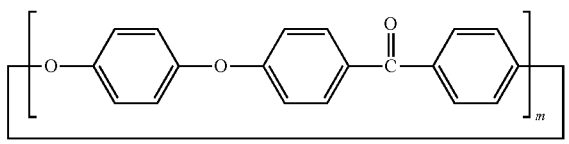
(I)

wherein, m represents an integer of 2 to 40;
said cyclic poly (phenylene ether ether ketone) being a mixture of cyclic poly (phenylene ether ether ketone)s having different repeating numbers (m) and said composition having a melting point of not higher than 270° C.

18. The cyclic poly (phenylene ether ether ketone) composition according to claim 17, wherein base (A) is carbonate and/or bicarbonate.

19. A cyclic poly (phenylene ether ether ketone) composition produced according to a method of producing the cyclic poly (phenylene ether ether ketone) composition, which is characterized in that, when a mixture (M2) comprising at least a linear poly (phenylene ether ether ketone) represented by the following Formula (II):

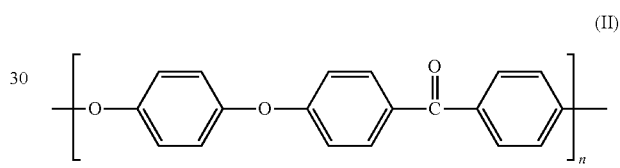
(II)

a dihalogenated aromatic ketone compound, a dihydroxy aromatic compound, a base (A) and an organic polar solvent is loaded at once and then heated to react to produce said cyclic poly (phenylene ether ether ketone) composition, said organic polar solvent is used in an amount of not less than 1.20 L and not more than 10 L with respect to 1.0 mol of benzene ring component in said mixture (M2), wherein the cyclic poly (phenylene ether ether ketone) composition, which comprises not less than 60% by weight of a cyclic poly (phenylene ether ether ketone) represented by the following Formula (I):

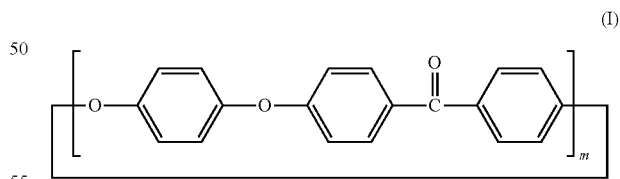
(I)

wherein, m represents an integer of 2 to 40;
said cyclic poly (phenylene ether ether ketone) being a mixture of cyclic poly (phenylene ether ether ketone)s having different repeating numbers (m) and said composition having a melting point of not higher than 270° C.

20. The cyclic poly (phenylene ether ether ketone) composition according to claim 19, wherein base (A) is carbonate and/or bicarbonate.

* * * * *